US006261781B1

(12) United States Patent
Kolesar

(10) Patent No.: US 6,261,781 B1
(45) Date of Patent: *Jul. 17, 2001

(54) DIRECT DETECTION AND MUTATION ANALYSIS OF LOW COPY NUMBER NUCLEIC ACIDS

(75) Inventor: Jill M. Kolesar, Cross Plains, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/499,003

(22) Filed: Feb. 4, 2000

Related U.S. Application Data

(63) Continuation-in-part of application No. 09/481,822, filed on Jan. 11, 2000, now abandoned, and a continuation-in-part of application No. PCT/US98/16347, filed on Aug. 5, 1998, which is a continuation of application No. 08/906,443, filed on Aug. 5, 1997, now Pat. No. 6,013,442.

(51) Int. Cl.[7] .................................................... C12Q 1/68
(52) U.S. Cl. .............................................. 435/6; 435/91.2
(58) Field of Search ................................. 435/5, 6, 91.2, 435/91.1; 536/26.6

(56) References Cited

FOREIGN PATENT DOCUMENTS

| 0 382 433 A2 | 2/1990 | (EP) . |
| 0 714 986 A1 | 5/1996 | (EP) . |
| WO 93/13223 | 8/1993 | (WO) . |

OTHER PUBLICATIONS

Database WPI, Section Ch, Week 9131, Derwent Publications Ltd., London, GB; Class B04, AN 91–227685, XP002084014 & JP 03 147797 A (Shimadzu Corp), Jun. 24, 1991, see abstract.

Fang C., et al., "Sequence–Dependent Separation of DNA Fragments by Capillary Electrophoresis in the Presence of SYBR® Green I", BioTechniques, vol. 23, Jul. 1997, pp. 58, 60.

Kolesar J.M., et al., "Direct quantificaion of HIV–1 RNA by capillary eletrophoresis with laser–induced fluorescence", Journal of Chromatography B, vol. 697, Sep. 12, 1997, pp. 189–194.

Coste et al., Comparative Evaluation of Three Assays for the Quantitation of Human Immunodeficiency Virus Type 1RNA in Plasman, J. Med. Virol. 50:234–302 (1996).

Schuurman et al., Multicenter Comparison of Three Commercial Methods for Quantification of Human Immunodeficiency Virus Type 1 RNA in Plasma, J. Clin. Microbiol. 34(12): 3016–22 (1996).

Mellors et al., Quantitation of HIV–1 RNA in Plasma Predicts Outcome after Seroconversions Ann. Intern. Med. 122:573–79 (1995).

Bianchi et al., Capillary Electrophoresis: Detection of Hybridization Between Synthetic Oligonucleotides and HIV–1 Gernomic DNA Amplified by Polymerase–Chain Reaction, J. Virol. Meth. 47:321–29 (1994).

Todd et al., Quantification of Human Immunodeficiency Virus Plasma RNA By Branched DNA and Reverse Transcription Coupled Polymerase Chain Reaction Assay methods; A Critical Evaluation of Accuracy and Reproducibility; Serodiagn. Immunother. Infect. Disease 6(4):233–39 (1994).

Fernandez–Arcas et al., Direct Quantification of HIV–1 RNA in Human Plasma by Free Solution Capillary Electrophoresis, J. Acq. Imm. Defic. Syn. Human Retrovir. 12:107–11 (1996).

Schwartz and Ulfelder, Capillary Electrophoresis with Laser–Induced Fluorescence Detection of PCR Fragments Using Thiazole Orange, Anal. Chem. 64:1737–40 (1992).

*Primary Examiner*—Eggerton A. Campbell
(74) *Attorney, Agent, or Firm*—Michael Best & Friedrich LLP; Teresa J. Welch

(57) ABSTRACT

A direct detection and quantitation of RNA or DNA contained in a sample is obtained by capillary electrophoresis of the RNA or DNA hybridized to a DNA or RNA probe of complementary sequence stabilized by the combination of a fluorophore terminally conjugated to the probe and a dye intercalating the RNA-DNA or DNA-DNA hybrid so formed. The RNA or DNA is quantified by measuring the total fluorescence emitted by the electrophoresed hybrid upon excitation by a laser generated light beam.

19 Claims, 16 Drawing Sheets

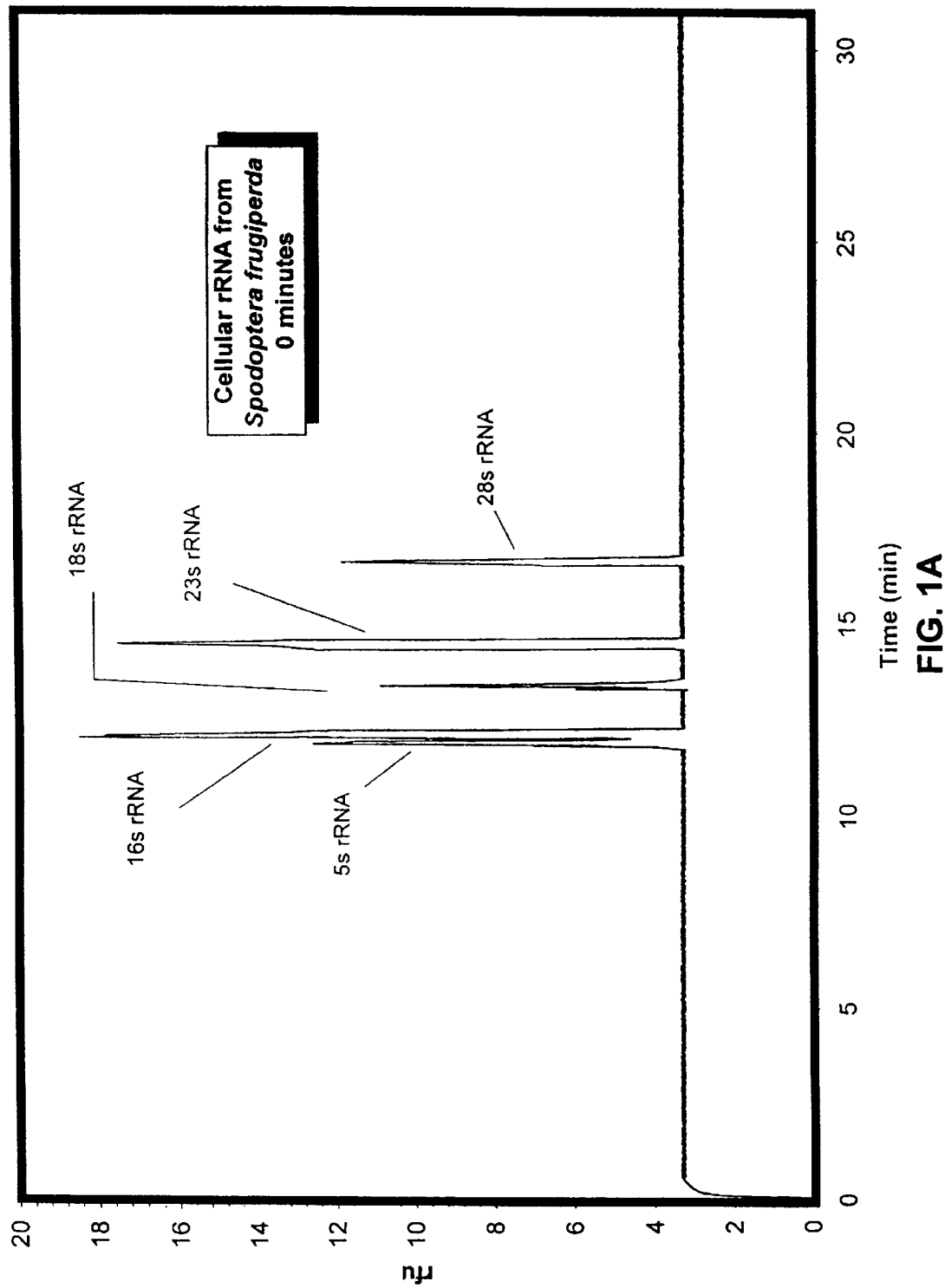

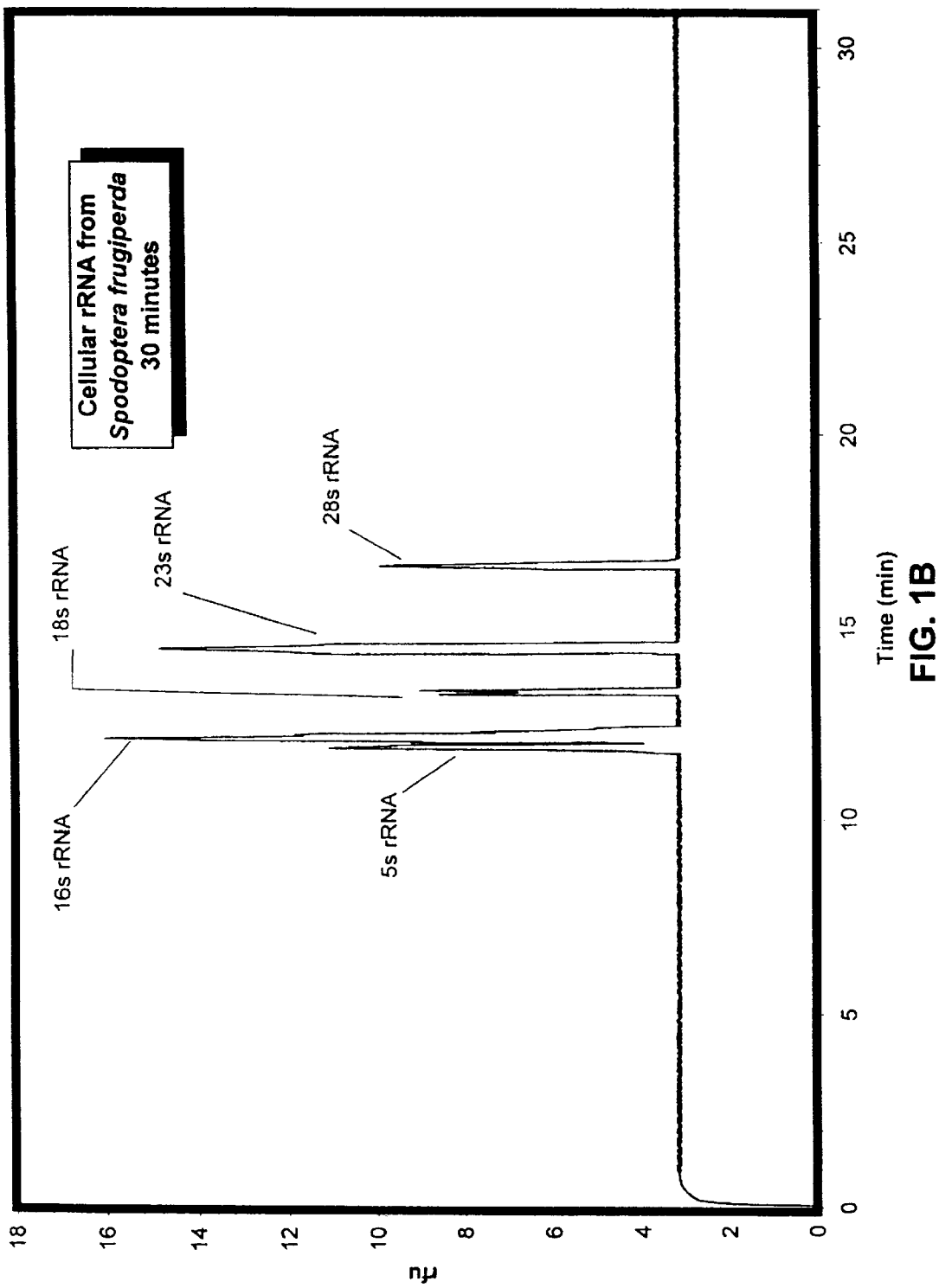

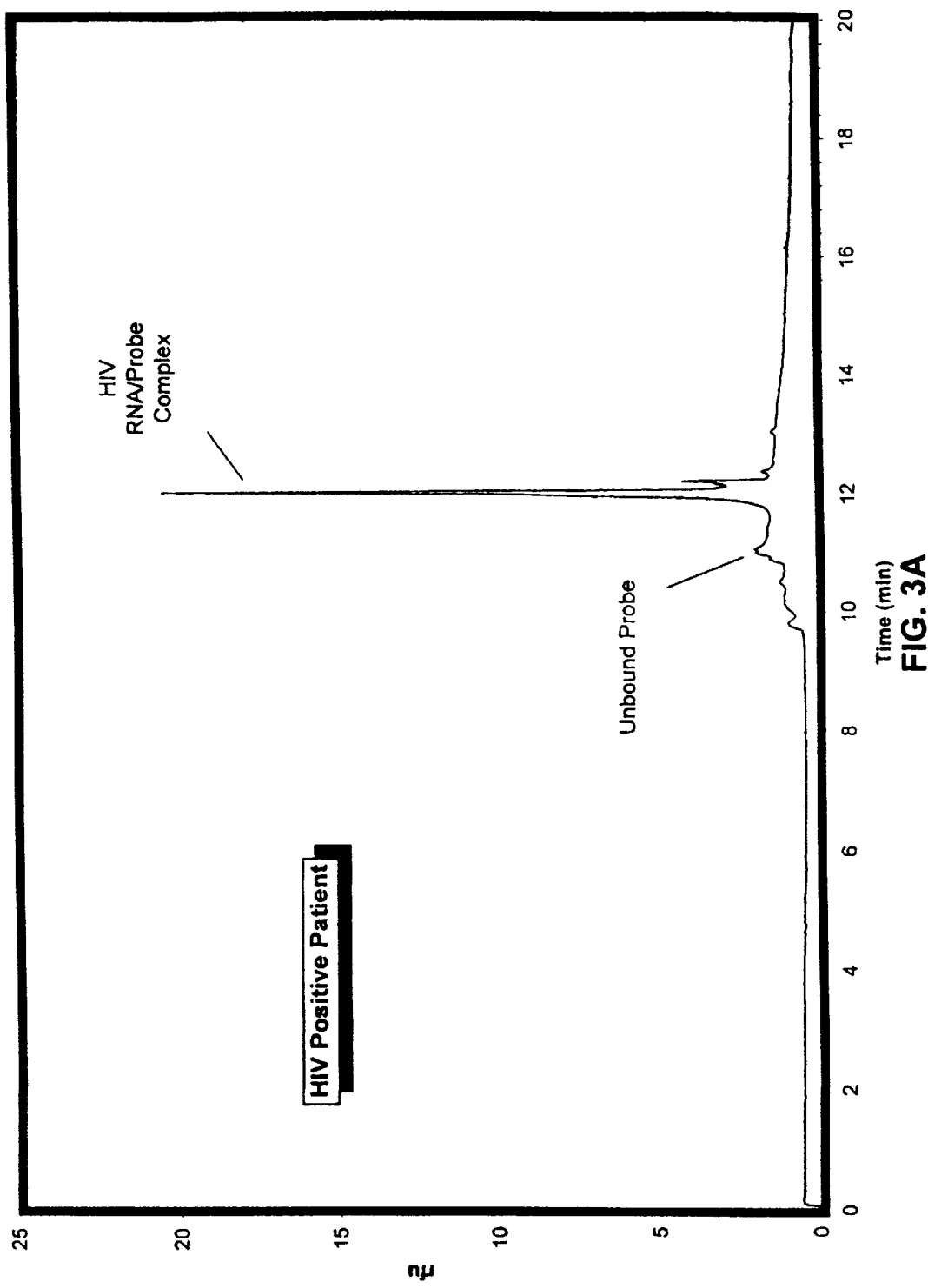

LNCap RNA Hybrid (NQO1-)

MCF7 RNA Hybrid (NQO1+)

SEQUENCE LISTING

<160> NUMBER OF SEQ ID NOS: 17

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
acagtattag aagaaatgaa tttgcc                                            26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
ggcaaaaaca tatcttctaa tactgt                                            26

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 3
tcggacctct atgccatgaa ct                                                22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4
agttcatggc atagaggtcc ga                                                22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5
aggctggttt gagcgagtgt tc                                                22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
gaacactcgc tcaaaccagc ct                                                22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7
cagcagacgc ccgaattcaa at                                                22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
atttgaattc gggcgtctgc tg                                                22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
agagacctcg agatgaggat ga                                                22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
tcatcctcat ctcgaggtct ct                                                22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 11
tctcgtattt ctgccagtcc tt                                                22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 12

```
aaggactggc agaaatacga ga                                            22

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 13
acagtattag aagayatgrr tttgcc                                        26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 14
agttgaaaca gcaagagact caaag                                         25

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
atttgaattc gggcgtctgc tg                                            22

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
ccgaaggttg aatcttggac ttgactg                                       27

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 17
ccgaaggttg aatcttagac ttgactgtat atcgtaa                            37
```

DIRECT DETECTION AND MUTATION ANALYSIS OF LOW COPY NUMBER NUCLEIC ACIDS

CROSS REFERENCE TO RELATED APPLICATIONS

This application is a continuation-in-part of U.S. Ser. No. 09/481,822, filed Jan. 11, 2000, now abandoned, which is a continuation of U.S. Ser. No. 08/906,443, filed Aug. 5, 1997, now U.S. Pat. No. 6,013,442 and is a continuation-in-part of International Application No. PCT/US98/16347, filed Aug. 5, 1998.

STATEMENT REGARDING FEDERALLY SPONSORED RESEARCH OR DEVELOPMENT

Not applicable.

BACKGROUND OF THE INVENTION

This invention relates to direct nucleic acid detection, particularly DNA and RNA in low copy number, without a requirement for amplification of the DNA or RNA molecules. The method is directly quantitative, utilizing capillary electrophoresis and laser-induced fluorescence to detect a target DNA-DNA or RNA-DNA probe hybrid band. The invention also relates to analysis of deletion and point mutations.

The quantitation of RNA and DNA derived from infectious agents or from cellular sources is important in the diagnosis and monitoring of a range of disease states. For example, the HIV viral load detected in serum of AIDS patients correlates to high concentrations of virus in the lymph nodes and has predictive value in assessing progression of the disease to advanced stages (see, e.g., Ho, et al., *Nature*, 373:123 (1995); Mellors, et al., *Ann. Intern. Med.*, 123:573 (1996)). Viral titers in serum are also correlated with disease progression for other viruses such as hepatitis C virus (HCV), nonA nonB hepatitis virus other than HCV, and atypical lentiviruses. The ability to quantify the copy number of DNA (or RNA) may also be useful in the diagnosis and prognostic evaluation of certain cancers. It is increasingly understood that all cancers are multi-step genetic diseases, and a number of genetic defects have been identified, e.g., in pancreatic cancer. Early stage detection of the mutated sequences can be an important tool in a treatment arsenal, but requires quantitation of DNA (or RNA) in low copy number.

The current methods for detecting RNA and DNA quantitation in low copy number are divided into two categories; (i) those that result in the amplification of the target sequence, and (ii) those that result in amplification of a signal sequence. Amplification of the target or signal sequence increases its numbers exponentially but the final result depends upon a large number of reactions that must occur in correct sequence. The coefficients of variability (CV) may often exceed 20% or more, so that the result obtained is unreliable, and does not correlate with, e.g., the stage of disease. The coefficient of variability (CV) is defined as the standard deviation of the values obtained divided by the mean. In any detection technique, a coefficient of variability (CV) of less than 15% is the accepted standard of accuracy.

Additionally, direct measurement of RNA in low copy number in a native sample, even where adequate detection sensitivities can be achieved, is thwarted by the inherent instability of RNA-DNA duplexes. Increasing the length of the hybridized target has been found to increase both sensitivity and stability of the hybrid, but the additional nucleotide sequence combinations increase the chance of non-specific hybridizing to fragments of host nucleic acids or partial hybridization to nonselected regions of the subject genome, thereby contributing to a falsely inflated positive value. Most of the improvements to date in low RNA copy number quantitation represent attempts to better control the multiple molecular events involved in signal or target amplification strategies.

Three main amplification systems currently available include branched chain signal amplification (bDNA), polymerase chain reaction (PCR) or in the case of a RNA target, reverse transsscriptase polymerase chain reaction (RT-PCR), and nucleic acid sequence-based amplification (NASBA). When detection of target RNA is the object, bDNA and RT-PCR involve a first reaction step that converts the system from an RNA target to a DNA target. bDNA involves an isothermal two-step hybridization approach.

An initial probe hybridizing with a complementary probe contains a plurality of noncomplementary sites capable of hybridizing to further DNA strands, which in turn may hybridize sites noncomplementary to the probe sequence. As repeated layers of hybridization occur, a branched DNA structure of extreme complexity is created. The last to be annealed strand in the branched structure carries a reporter. The original DNA target molecule thus gives rise to an amplification of the signal generating capability of the system. A full explanation and description of the bDNA technique is set forth in Fultz, et al., "Quantitation of plasma HIV-I RNA using an ultra sensitive branched DNA (bDNA) assay", in *Program and Abstracts of the 2nd National Conference on Human Retroviruses* (1995), and product literature, L-6170 Rev. 5.0 for the Quantiplex™ HIV-RNA Assay (Chiron Corporation).

In PCR, selected primers are used to define the left and right ends of the target sequence. In RT-PCR, a cDNA is generated from the RNA template, and then an ordinary PCR amplification ensues utilizing left and right primers. Each successive round of synthesis and thermal denaturation causes an exponential increase in the number of progeny strands generated in the system. After the amplification is complete, a probe having a complementary sequence to some portion of the amplicon and carrying a reporter can be used for detecting the amplified target.

In both RT-PCR and bDNA, the original RNA target can theoretically be dispensed with, without impairing the sensitivity of the test, once the conversion to a DNA system has occurred. These methods effectively circumvent the inherent lability of the RNA target or its RNA-DNA duplex hybrid.

PCR, RT-PCR and bDNA share many of the same deficiencies. The systems rely upon the integrity of a large number of successive hybridization events. If an early hybridization event fails for any of a number of reasons such as structural (steric) hindrance, uncorrected mismatch, binding of a defective enzyme molecule, etc., the final number of copies, and therefore, the intensity of the signal will be ablated. These random occurrences help to account for the great sensitivity of the assays coupled with a widely variable CV. Commercial assays normalize variability by co-amplification of an internal standard. To control for variability, an internal standard must be amplified under the identical conditions as the target, yet must be differentiated from the target, an almost impossible task. Introducing an internal standard, however, changes the PCR reaction kinetics itself. Additionally, RT-PCR, while showing some efficacy, is very labor intensive, and not practical under normal clinical laboratory conditions. Furthermore, the use of these systems for mutation analysis is especially problematic because the systems arbitrarily introduce new mutations and routinely incorporate incorrect bases, thus, giving a false positive rate.

NASBA is an isothermal assay which uses a combination of three enzymes and flanking primers to generate multiple RNA copies of original RNA/DNA targets. Each of these serves as a new template for transcription and DNA synthesis steps. The process is initiated upon annealing of two primers, one of which contains a phage promoter, which in the ensuing cDNA provides a point of initiation for transcription. Unlike PCR where the numbers of actual cycles of amplification are nominally controlled by the number of temperature cycles, there is much less control in NASBA. The technique suffers from a lack of uniformity between different target sequences, and in the same target sequence from one run to another. The commercial form of the assay employs three internal calibrators, which are co-amplified with the target sequence.

Three techniques, bDNA, NASBA and RT-PCR described herein were recently compared in a study by Coste, et al., *J. Med. Viro.*, 50: 293 (1996). bDNA was found to be most reproducible with CVs ranging from 6–35%. Better results were achieved at high copy number, 12.4% vs. 31% for low copy number. However, sensitivity was only 68% with a lower level of detection at, e.g., 4000 HIV equivalents. NASBA was the least reliable test with CVs ranging from 13–62%, with CV averages of 20.7% for high copy number and 41.8% for low copy number. Sensitivity was 100% with a lower level of detection at, e.g., 2600 HIV equivalents. RT-PCR had a sensitivity of 93%, but a mean CV of 43%.

For detection of mutations, single strand conformational polymorphism (SSCP) is the most common technique used to evaluate small mutations in DNA, usually a single base change. This technique is based on the premise that DNA fragments varying by a single base pair will have altered migration patterns on gel electrophoresis. The great benefit of SSCP is that unknown single nucleotide mutations (SNPs) can be detected by this methodology.

To perform SSCP, the target sequence of DNA is simultaneously amplified by PCR and labeled with radioactivity. The PCR product is then heated to disassociate the strands and electrophoresed on nondenaturing polyacrylamide gels. Control DNA, without any mutations, is electrophoresed to determine the migration time. If the sample DNA has the same nucleotide sequence as the control DNA, a single band is present. However, if a mutation is present two bands, with differing migration times will be present.

Currently, SSCP relies almost exclusively on PCR. As noted hereinbefore, PCR utilizes exponential amplification, with the gene concentration after such amplification being determined easily and reliably by standard methods. However, the initial gene concentration present in a given sample, can not be determined by routine PCR. Methods involving internal standards and standardized visualization have been employed. Unfortunately, these methods have rarely been validated, and reported CV's range from 18–97%, making these PCR-based methods of limited value in clinical and diagnostic settings.

The other major limitation of PCR, particularly in the context of mutation detection, is the rate of error incorporation. The thermostable DNA polymerase derived from Pyrococcus furiosus (Pfu) is reported to have the lowest average error rate. This enzyme makes an error (i.e., introduces a mutation) every $6.5 \times 10^7$ base pairs synthesized. Assuming a single copy gene, a 300 base pair product and 40 cycles of amplification, this enzyme can be expected to introduce approximately two mutations in every PCR reaction. Standard sequencing techniques require 8 PCR reactions to sequence a 300 bp fragment. Using Pfu polymerase, at least 16 mutations will be introduced when sequencing this fragment. Additionally, since the coding (cDNA) region of most genes is greater than 2000 bp, a minimum of 48 PCRs, (with 96 new mutations introduced) is required to sequence a single gene. This rate of mutation incorporation is unacceptably high, as clinically significant point mutations are usually present in fractions at or below 1 in $10^6$.

This rate of mutation incorporation is especially problematic in evaluating solid tumors. Unlike hematologic malignancies, where clonal expansion, or where a single cancerous cell multiplies to make billions of identical cancer cells, the mutation spectrum in solid tumors is heterogenous and the genetic make-up of individual cells within the tumor is different. At least six different mutations are expected per solid tumor and an individual cell will have some, all or none of the mutations. An additional problem when evaluating clinical tumor samples is the difficulty in obtaining only tumor cells in a given sample. Biopsy samples may contain normal tissue, immunologic infiltrates and precursor lesions as well as the tumor itself. The presence and frequency of these mutations within a tumor will be essential to evaluate when considering the influence of genetic make-up on prognosis, diagnosis and therapeutic decisions.

Despite improvements in the foregoing techniques that may result from optimization of the operating conditions of the assays, and from discovery of reagent combinations that minimize interferences with hybridizations, few rapid, simple, reliable and accurate quantitative methods are available. It is unlikely that variability of existing methods will ever be reduced uniformly to CV values of less than 15%. Priming errors, hybridization interferences and introduction of new mutations cannot be entirely overcome, and misevents occurring early in the sequence of amplification steps have a geometric impact on the result. Even if the level of sensitivity for direct detection of DNA and RNA could be increased by several orders of magnitude over standard UV detection methods, and if the problem of RNA-DNA duplex instability could be solved, fully quantitative direct detection of DNA and RNA sequences, including mutated gene sequences, would provide a viable alternative to current amplification-based methods without introduction of new mutations.

SUMMARY OF THE INVENTION

The present invention provides a method of direct detection of DNA and RNA target sequences, including mutated sequences with deletion or point mutations. The method utilizes capillary electrophoresis and laser-induced fluorescence (CE-LIF) to detect a hybrid formed between a target DNA or RNA molecule and a complementary DNA or RNA probe. The method of the present invention eliminates an amplification step by relying on free solution hybridization of target nucleic acid with specific probes, followed by the CE-LIF analysis. Elimination of the amplification step by direct detection represents an important advance over PCR for applications requiring quantitation or highly accurate analysis (e.g.: no mutation incorporation) such as SSCP. Since there is no amplification step, direct quantitation is possible and no mutations are introduced by the process.

The method according to the present invention has excellent potential for high through-put and automation. The method has an accuracy superior to methods requiring amplification and is also of lower cost than amplification-based tests. The method of the present invention is fast, highly reliable and has a low coefficient of variability even at low copy number. The method has greater sensitivity than virtually any other direct gene quantitation method.

The foregoing and other advantages of the present invention are seen in an aspect thereof in a method of detecting nucleic acid sequences, i.e., RNA or DNA, in low copy number. The method of direct detection of a target nucleotide sequence in accordance with the present invention comprises mixing a portion of a sample comprising unamplified nucleic acid molecules isolated from a biological source with a fluorescent polynucleotide probe under hybridizing conditions, the probe having a nucleotide sequence complementary to at least a portion of the target sequence; applying a portion of the hybridization mixture to a capillary electrophoresis column; electrophoresing the nucleic acids molecules in the column in the presence of a dye capable of intercalating double stranded nucleic acids, the electrophoresis conducted for a period of time and under conditions suitable to allow size fractionation of the nucleic acid molecules; and measuring the fluorescent intensity of light emitted from column upon excitation by laser-induced fluorescence.

In another aspect of the invention, the foregoing method can be used to detect and quantitate a gene sequence e.g., one in which a deletion mutation is present.

In a further aspect, the invention provides a method for detecting the presence or absence of a point mutation. The method for directly detecting the presence or absence of a point mutation in a target sequence in a sample comprising unamplified nucleic acid isolated from a biological source, comprising the steps of: (a) mixing a portion of the sample with a polynucleotide probe preparation comprising a first fluorescent polynucleotide probe complementary to a mutated target sequence under hybridizing conditions; (b) applying a portion of the mixture of step (a) to a capillary electrophoresis column; (c) electrophoresing the nucleic acids in the capillary column of step (b) in the presence of a dye capable of intercalating double stranded nucleic acids, the electrophoresis conducted for a period of time and under conditions suitable to allow size fractionation of the nucleic acids; and (d) measuring the fluorescent intensity of light emitted from column upon excitation by laser-induced fluorescence. The probe preparation further comprises a second fluorescent polynucleotide probe complementary to the wild-type sequence corresponding to the mutated sequences, the length of the second probe being different from the length of the first probe.

The present invention also provides kits containing the key ingredients for directly detecting or quantitating RNA and DNA sequences suspected of being present in a biological specimen, utilizing capillary electrophoresis and laser-induced fluorescence. Each kit contains a quantity of a polynucleotide probe labeled with a fluorophore at its 3' terminus, its 5' terminus, or at both termini, whose sequence is complementary to a target DNA or RNA sequence.

The kit also provides a quantity of a fluorescent dye capable of intercalating an nucleic acid hybrid molecule. Preferably, the vessels containing the reagent probe and dye are made of materials to which the reagents do not adhere, such as surface-treated borosilicate glass, polypropylene and the like, and are shaped to accommodate an automatic pipetter tip.

Other advantages and a fuller appreciation of specific adaptions, compositional variations and physical attributes will be gained upon an examination of the following detailed description of preferred embodiments, and the appended claims taken in conjunction with the figures of the drawing. it is expressly understood that the drawings are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawing wherein any like designations refer to like elements through and in which:

FIGS. 1A–1C are electropherograms of cellular RNA obtained from *Spodoptera frugiperda* culture at different injection times;

FIGS. 3A–3C show an electropherogram analysis of hybridization products, using the HIV specific probe of FIG. 2;

FIG. 4A is the control showing migration of the probe at 8–9 minutes. FIG. 4B shows the DNA/DNA hybrid peak migrating at about 11.5 minutes;

DETAILED DESCRIPTION OF THE PREFERRED EMBODIMENT

Figure 1C:
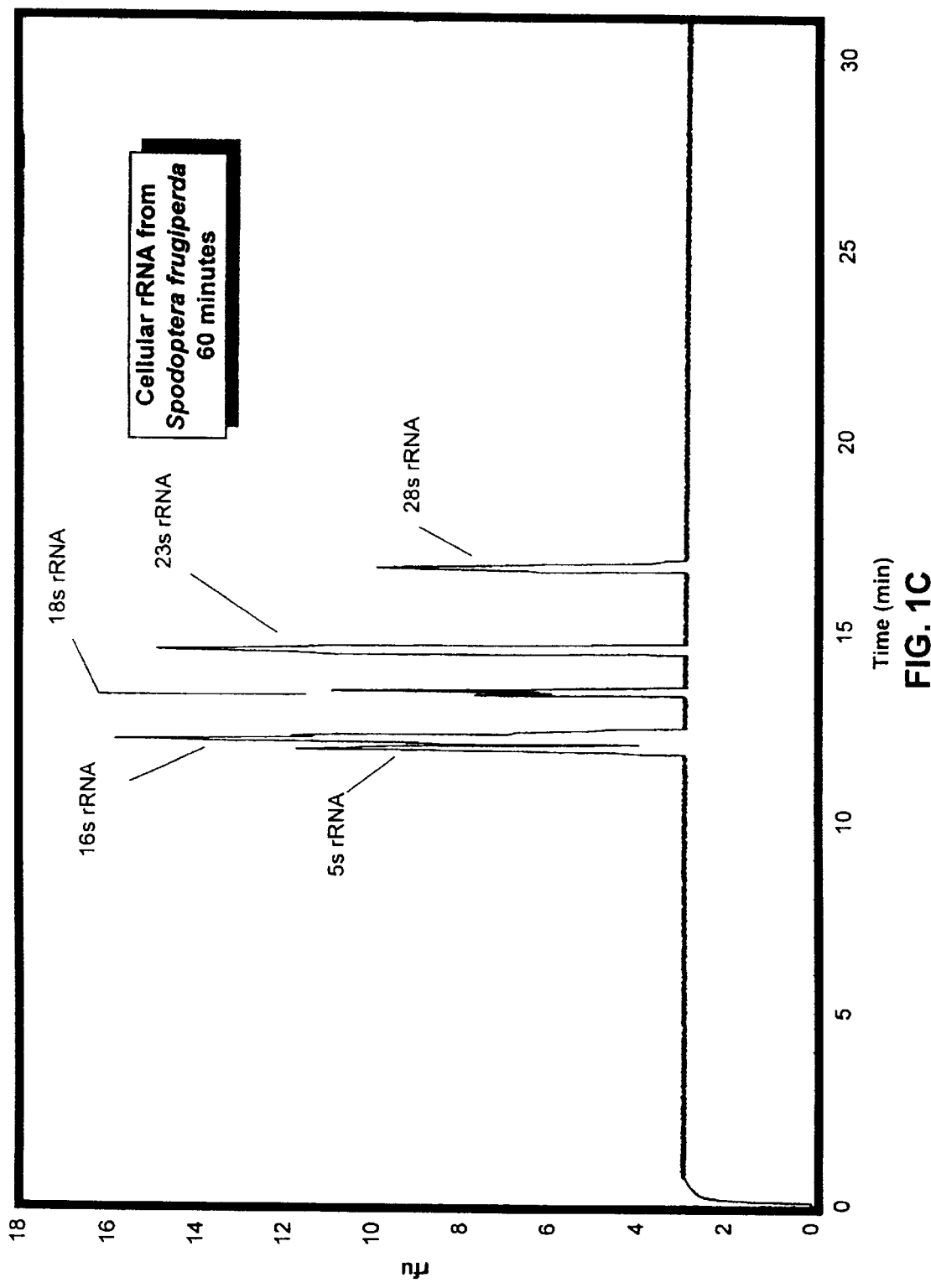

The present invention relates to a method of direct detection of nucleic acid sequences in low copy number without the need for amplification. The method is highly reliable, has an accuracy greater than the methods requiring amplification, has a low coefficient of variability, and has greater sensitivity than virtually any other direct gene quantitation method. The present invention is suitably used for direct detection of RNA and DNA as well as detection and analysis of mutated sequences. The method in accordance with the present invention also overcomes the extreme lability of target RNA-DNA duplexes under conditions of electrophoresis. Accordingly, the present invention will now be described in detail with respect to such endeavors. Those skilled in the art will appreciate that such description of the invention is meant to be exemplary only and should not be viewed as limitative of the full scope thereof.

In the following description of the method of the invention, process steps are carried out at room temperature and atmospheric pressure unless otherwise specified.

The method in accordance with the present invention includes applying a hybrid of a fluorophore-labeled polynucleotide probe and the nucleic acid sequence of interest to a capillary electrophoresis column, the gel buffer for which contains a dye capable of intercalating double stranded nucleic acids, and measuring the fluorescent intensity of light emitted by the hybrid upon excitation by laser-induced fluorescence.

In the capillary electrophoresis step, the sample containing the DNA-DNA or DNA-RNA hybrid is hydrodynamically injected across a capillary filled with a gel, particularly a polyacrylamide, and separation is performed under constant voltage. The dye in the gel buffer is capable of intercalating the hybrid, binding to the interstices of the duplex, so that these intercalated molecules migrate with the hybrid band. The unbound dye molecules are not seen as background because their quantum yield varies in the presence of nucleic acid. The band is quantitated by directing a laser-induction beam along the gel. The hybrids with pendant dye (both covalently attached and bound by electrostatic interaction), migrating as a band, absorb the light of excitation wavelength, and emit at a lower energy wavelength. Peak areas of light emission intensity are identified. The total fluorescence is the sum of the fluorescence values under the peak.

It has been found that terminal labeling of the DNA probe with one dye type and intercalating the duplex hybrid with a second dye type has the unexpected benefit of dramatically increasing the stability of the hybrid; this is especially significant for the inherently labile RNA-DNA hybrid. Hence, the present invention provides a method for stabilizing during capillary electrophoresis, nucleic acid hybrids comprising polynucleotide target strand and a fluorophore terminally labeled polynucleotide probe strand which involves electrophoresing the nucleic acid hybrid in the presence of an intercalating dye. Any dye, which preferably fluoresces at the same wavelength as the dye covalently attached to the DNA probe and is capable of intercalating double stranded nucleic acids, will be efficacious in increasing stability. The ability to stabilize short DNA-RNA duplexes means that a RNA target sequence can now be readily selected having less than 5% homology (i.e., sequence similarity) to any other portion of the target and non-homology to host nucleic acids, as verified by a GenBank search or by comparison to other published sequence databases.

Detection of RNA

A basic problem in direct gene quantitation which has been overcome by the present invention is the extreme lability of target RNA-DNA duplexes under conditions of electrophoresis. Interestingly, the use of carrier RNA to stabilize the target RNA and the double stranded nucleic acid of the hybrid, is unavailing. Experiments utilizing carrier RNA, as set forth in Example 3, Table 4, show that there is no stabilization of the RNA-DNA hybrid having the sequence of Seq. I.D. No. 1 in the presence of carrier. Normally, carrier nucleic acid or protein, in the case of proteinaceous targets, function as a coprecipitant, or compete for a degradative enzyme, thereby protecting the target species through shear overwhelming numbers. Failure of carrier RNA to mitigate degradation of the hybrid is consistent with the conclusion that the RNA-DNA hybrid of short length is inherently unstable, and its lability is not due to a contaminating nuclease, or other process for which a carrier population can exert protection or rescue. Since the lability appears to be activated by the electric current, separation of tRNA from duplex may cause a loss of whatever protection might otherwise be afforded.

In the method of the present invention, isolating RNA from biological specimens may be carried out by any conventional method which takes precautions in minimizing RNA degradation. Accordingly, procedures involving heat or strong acid/base reagents are to be avoided. In preparing specimens from serum, blood is centrifuged to remove cells, and then extracted. There are several extraction kits commercially available for this purpose, e.g., the Ultraspec II RNA isolation system from Biotecx, Houston, Tex.

The probe sequence is selected for uniqueness within the genome of the organism to be detected and monitored, and which is unlikely to show any homology for the host genome. Lack of homology, is important because it is impossible to guarantee that all cells contained in the specimen will be removed by centrifugation. The degree of homology between the probe sequence and the remainder of the target genome should be as low as possible, but less than 5%. Thus, it is important to select a probe sequence long enough to confer selectivity and short enough to avoid partial homologies with non-target RNAs.

The probes employed in the Examples provided below were DNA probes. It is reasonably expected that RNA probes would be equally suitable for use in the practice of the present invention, although DNA probes are generally more economical.

The DNA probe will suitably have a nucleotide sequence of about 15 to 50 bases, preferably between 20 and 30 bases. In the case of HIV-1, a unique, genetically stable 26 base sequence from the polgene was selected, having the sequence 5'-AGTATTAGAAGAYATGRRTTTGCC-3' (Seq. I.D. No. 1) (in which Y=A or C; and R=A or G). This sequence is identified in GenBank as entry U62632. A probe terminally labeled with a fluorophore at the 5' end and having the sequence given above which is complementary to the HIV-1 sense strand was prepared synthetically utilizing 5'-fluorescein phosphoramidite. Another sequence of interest in HIV quantitation is: 5'-GGCAAARRCATYTCTTCTAATACTGT-3' (Seq. I.D. No. 2). Also, the following sequences are useful in the present invention for quantitation of NAD(P)H: Quinone oxidoreductase and Human Topoisomerase I, respectively.

NAD(P)H: Quinone oxidoreductase

5'-TCGGACCTCTATGCCATGAACT-3' Seq. I.D. No. 3

5'-AGTTCATGGCATAGAGGTCCGA-3' Seq. I.D. No. 4

5'-AGGCTGGTTTGAGCGAGTGTTC-3' Seq. I.D. No. 5

5'-GAACACTCGCTCAAACCAGCCT-3' Seq. I.D. No. 6

5'-CAGCAGACGCCCGAATTCAAAT-3' Seq. I.D. No. 7

5'-ATTTGAATTCGGGCGTCTGCTG-3' Seq. I.D. No. 8

Human Topoisomerase I:

5'-AGAGACCTCGAGATGAGGATGA-3' Seq. I.D. No. 9

5'-TCATCCTCATCTCGAGGTCTCT-3' Seq. I.D. No. 10
5'-TCTCGTATTTCTGCCAGTCCTT-3' Seq. I.D. No. 11
5'-AAGGACTGGCAGAAATACGAGA-3' Seq. I.D. No. 12

An intercalating fluorescent dye was also used to visualize a band of probed RNA migrating on an electrophoresis column, the dye being incorporated into the column gel. It was found, however, that for short (15–30) base pairs neither a fluorescein labeled DNA probed RNA duplex without intercalating dye, nor a non-terminally labeled DNA probed RNA duplex in the presence of an intercalating dye alone was stable during electrophoresis. However, the combination of a terminally fluorophore labeled DNA probe and the presence of an intercalating fluorescent dye produced remarkable stability of the duplex. In an alternate embodiment of the present method, the intercalating dye may be taken up by the DNA-RNA hybrid prior to loading on the gel.

The preferred terminal fluorophore is fluorescein, although others such as rhodamine, or the BODIPY series (Molecular Probes, Inc.) may be utilized. The preferred intercalating dye is thiazole orange, although other dyes such as YOYO (also available from Molecular Probes, Inc., and whose structure is given at p.155 of its 1996 Catalogue for Product No. Y-3601) may be used. When using a laser-induced detection system, it is preferable from a sensitivity standpoint, to use terminating and intercalating dye pairs which emit light at the same wavelength, thereby boosting the signal additively (see Table 3 in Example 1). Fluorescein and thiazole orange absorb at 488 nm and emit at 520 nm. For probe manufacture, fluorescein is ideal because of its ease of use, well known coupling chemistries, and its low cost.

While thiazole orange is more expensive, in the capillary mode of electrophoresis, the small volumes reduce usage.

Utilizing the combined dyes prevents degradation of the RNA-DNA hybrid, and also increases sensitivity to levels comparable to other methods. For example, for monitoring HIV, the most sensitive assay system will be the best system. With a lower detection limit of 50 attogram, the system of the present invention is more sensitive than other available methods. The lower limit of the linear range is 11 picograms to 72 femtograms, which provides a lower detection limit of 7200 HIV equivalents per mL compared to 10,000 equivalents for bDNA. The greater sensitivity of RT-PCR (350 equivalents/ml) has a precision of only 11–93%, whereas in the present method of direct detection, the CV is always less than 15% for peak area (total fluorescence). The precision (CV) of peak position in the gel (lapsed time) is less than 1%. In hybridization assays of actual patient specimens producing RNA-DNA hybrids, reliable and quantitative detection of less than 2000 equivalents of HIV could be achieved.

The technique of capillary electrophoresis (CE) is utilized in the present method to size-separate individual nucleotide sequences. A discussion of methods applicable to the Beckman instrument used in the experiments set forth in the Examples hereinbelow is given in Altria, et al., *Quantitative Applications of Capillary Electrophoresis in Pharmaceutical Analysis*, Beckman: 1994, Publication No. 538703, and Altria, *Capillary Electrophoresis Guidebook*, Humana Press: 1995. CE has been applied to direct quantitation of HIV-1 in patients having high serum levels of HIV-1. Ferandez-Arcas, et al., *J. Acq. Immune Defic. and Hum. Retrobiol.*, 12: 107 (1996) reported detection by direct UV analysis of extracted RNA at levels of greater than $10^8$ virions/mL correlated to the very high levels of circulating virus in early infection. This reported direct technique, even with the enhancement expected with laser-induced fluorescence, is not sensitive enough to monitor anti-HIV drug therapy where levels of circulating virus decline. For further comprehensive materials on conventional methods and applications of capillary electrophoresis, please see Landers, *Handbook of Capillary Electrophoresis*, CRC Press: 1997.

Detection of DNA

The direct detection to quantify DNA is carried out similarly to that for detection of RNA described hereinabove.

First, genomic DNA is obtained by standard methods, and digested with restriction enzymes to generate smaller fragments of DNA. Next, DNA is hybridized with a sequence specific, fluorescently labeled probe, generating a nucleotide complex or hybrid of probe and target DNA. As explained above, the probe may be DNA or RNA, although DNA probes are generally considered to be more economical. Finally, the complex is analyzed by CE-LIF. CE-LIF separates by molecular size and measures the fluorescent signal from the labeled probe as well as the dye, e.g., thiazole orange, present in the buffer, which intercalates into the nucleotide complex.

Detection of Mutations

The detection of mutations, both deletion and point mutations, utilizes the same general process steps described hereinabove.

In a preferred embodiment, direct detection of deletion mutations may most conveniently be performed as described in the Examples using a single polynucleotide probe specific for the gene of interest. As the Examples demonstrate, if the target gene sequence of interest is present, the probe will bind and be detected by CE-LIF. If the gene is absent, the probe will not bind and will migrate at the rate characteristic of unbound probe. Nucleotide software (e.g. DNAStar) and data bases (e.g., GenBank) are suitably used to identify unique sequences and to determine probe binding and reaction conditions.

Alternatively, one wishing to identify a deletion mutation may use more than one probe in the practice of the present invention. For example, it is envisioned that two probes from the intron region of the gene may be synthesized for use in detecting the presence or absence of the gene in a sample. Because the assay of the present invention is also quantitative, genotypic characterization (heterozygous or homozygous) of the mutation is possible. mRNA and DNA are extracted from the same sample and two probes from the exon or coding region of the gene are assigned, allowing measurement of the gene expression of the gene in the sample. A comparision of the intron gene quantity to the exon gene quantity provides information about the presence or absence of the gene, whether the gene is homozygously or heterozygously deleted, and whether the gene is expressed (mRNA).

To identify point mutations, a probe to the known wild-type sequence and a different probe to the mutant sequence are synthesized. The wild-type probe suitably binds to the wild-type gene and the mutant probe to the mutant gene (if present). Since the assay of the present invention is quantitative, a sample can be determined to by homozygous or heterozygous for the mutation. Stringency experiments were undertaken to determine binding conditions for the probes, varying both the hybridization buffer conditions as well as the hybridization temperatures.

The present invention is further explained by the following examples which should not be construed by way of limiting the scope of thereof.

All reagents were molecular biology grade and solutions (with the exception of CE buffers) were autoclaved prior to use. Glassware and disposable supplies were autoclaved prior to use.

EXAMPLE 1

Direct Detection of RNA

Sample Collection and RNA Extraction

For isolation of RNA from a HIV seropositive patient and seronegative volunteer, whole blood anticoagulated with heparin was collected and subjected to centrifugation at 3,000×g for 15 min at 4° C. on a Centra GP8R refrigerated centrifuge (International Equipment Corporation, Needham Heights, Mass., USA). The plasma was separated and stored at −80° C. RNA was extracted from plasma samples using the Ultraspec II RNA isolation system (Biotecx, Houston, Tex., USA) as recommended by the manufacturer. RNA was also extracted from both plasma and peripheral blood lymphocytes of the HIV seronegative normal volunteer. RNA was also obtained from *Spodoptera frugiperda* 21, grown in TC-100 serum (HyClone, Logan, Utah, USA) at 27° C. RNA was resuspended in DPEC-treated water (Biotecx, Houston, Tex., USA) and quantitated spectrophotometrically. Reference is made to FIGS. 1A–1C which are electropherograms of a sample of cellular RNA (1.856 µg/µL) obtained from *Spodoptera frugiperda* culture.

Probe Synthesis and Hybridization

Figure 2:
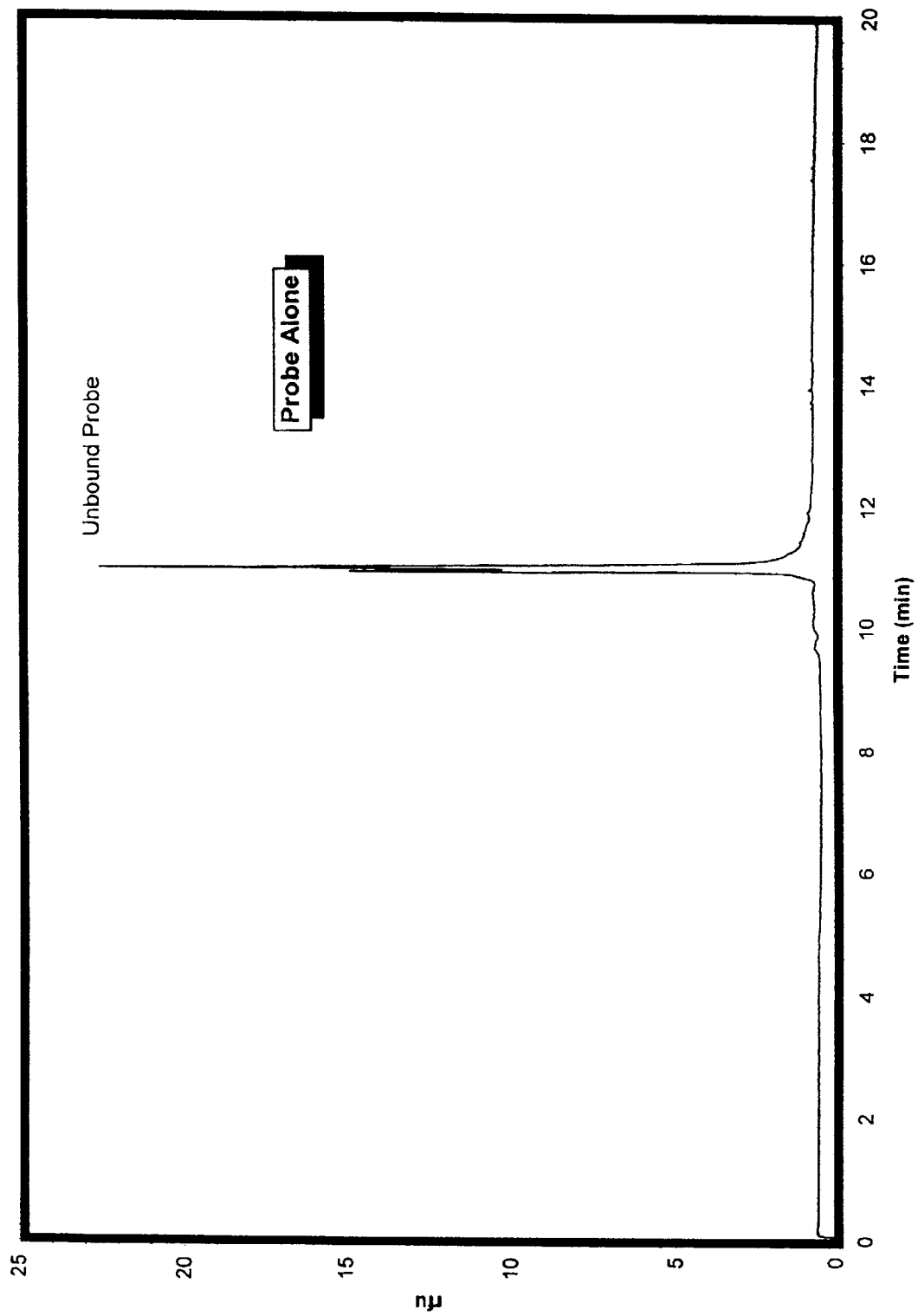
FIG. 2 is an electropherogram analysis of fluorescently labeled HIV specific probe.

To insure specificity, a unique gene sequence is probed. The pol region is the most genetically unique of the HIV genome and a 26 bp sequence in this region was selected (GenBank entry U62632). Uniqueness was verified by a GenBank search. A 5'-fluorescein phosphoramidite (Glenn Research, Sterling, Va., USA labeled DNA probe having the sequence 5'-ACAGTATTAGAAGAYATGRRTTTGCC-3') (SEQ ID NO:13) was synthesized by the University of Wisconsin Biotechnology Center (Madison, Wis., USA). See FIG. 2 which is an electropherogram analysis of the HIV specific probe alone diluted in DEPC-treated water to a concentration of 72 fg/7.1 nL, which elutes at 11 min.

Sample RNA present in a concentration of 0.095 µg/µL was diluted serially with DEPC-treated water and hybridized with the DNA probe (1.0125 µg) in a buffer volume of 30 µL containing 10 mM Tris-HCl (pH 7.2), 1 mM EDTA (pH 8.0), 50 mM NaCl, and 1 mM cetyltrimethylammonium bromide (CTAB) (ACROS, Pittsburgh, Pa., USA). The mixture was heated at 85° C. for 10 min, and then incubated at 42° C. for 4 h. The addition of CTAB to the hybridization, as reported by Pontius, et al., *Proc. Natl. Acad. Sci.*, 88:8237 (1991) increases intermolecular crowding and decreases by hybridization time.

Following incubation, samples were digested for 30 min at 37° C. with RNAase 1 (4.5 U) (Promega Corporation, Madison, Wis., USA) in 50 µL digestion buffer (50 mM Tris-HCl (pH 7.2), 5 mM EDTA (pH 8.0)). Samples were flash frozen at −80° C. to stop enzymatic digestion.

CE-LIF Analysis

Separations were performed on a P/ACE 2050 CE system (Beckman Instruments, Fullerton, Calif., USA) with the temperature held constant at 20° C. Detection of hybridization samples was achieved using laser-induced fluorescence in the reversed-polarity mode (anode at the detector side) at excitation of 488 nm and emission of 520 nm.

Samples were introduced hydrodynamically by 10 s injections at 0.34 Pa across a 65 cm×100 µm coated eCAP dsDNA capillary filled with replacable linear polyacrylamide (Beckman Instruments, Fullerton, Calif., USA). The capillary was conditioned with eCAP dsDNA 1000 gel buffer which contained 60 µL of LiFluor dsDNA 1000 EnhanceCE (thiazole orange) intercalator per 20 mL of buffer (Beckman Instruments, Fullerton, Calif., USA). Separations were performed under constant voltage at 7.0 kV for 15–30 min. The capillary was rinsed with gel buffer for 3 min prior to each injection. The capillary was calibrated with the fluorescently labeled probe and a mixture of RNA molecular markers (Ambion, Austin, Tex., USA). The 5 markers ranged in size from 100–500 bp. Post-run analysis of data was performed using the System Gold chromatography data system (Beckman Instruments, Fullerton, Calif., USA).

Figure 3B:
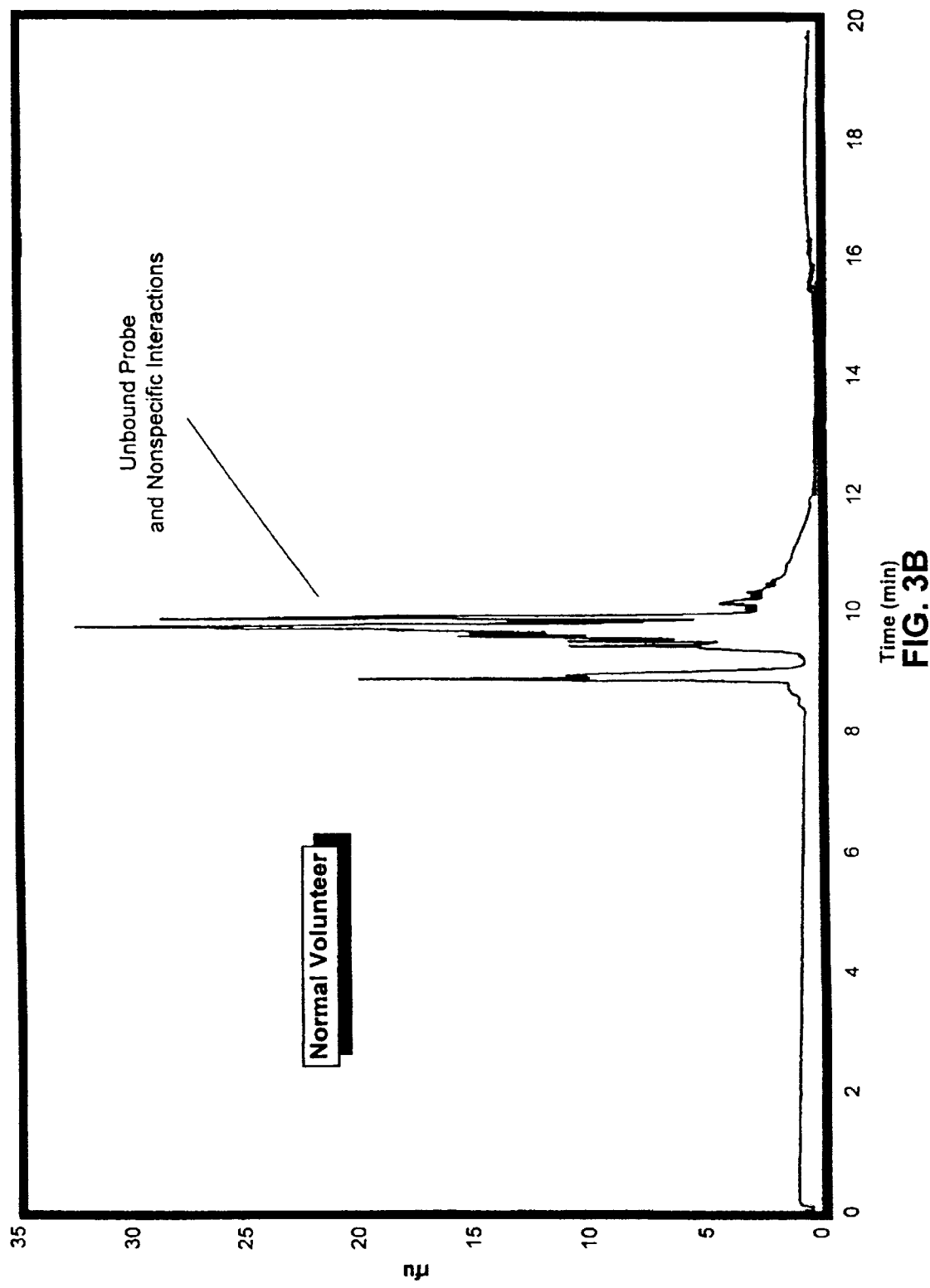
Figure 3C:
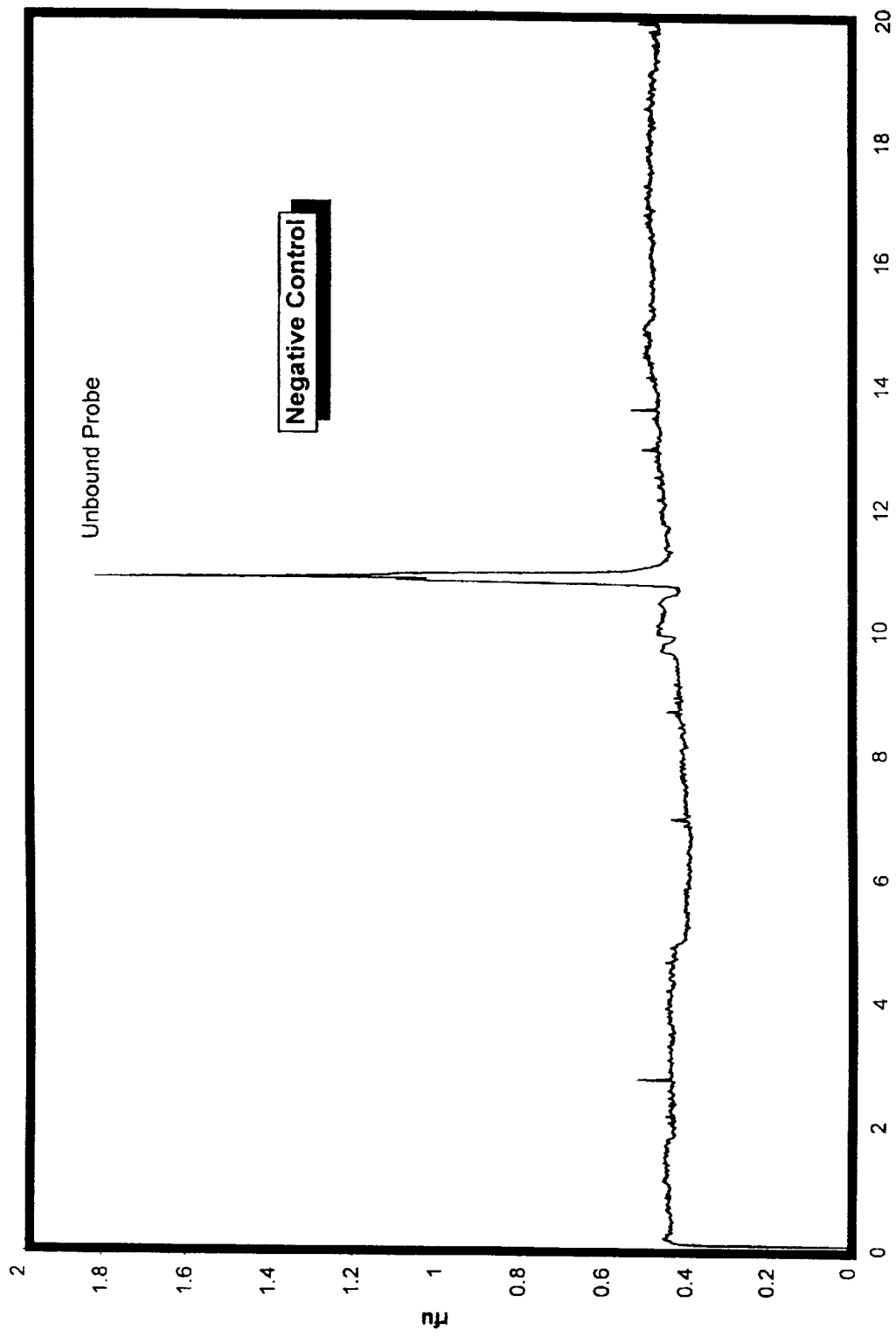
Figure 4A:
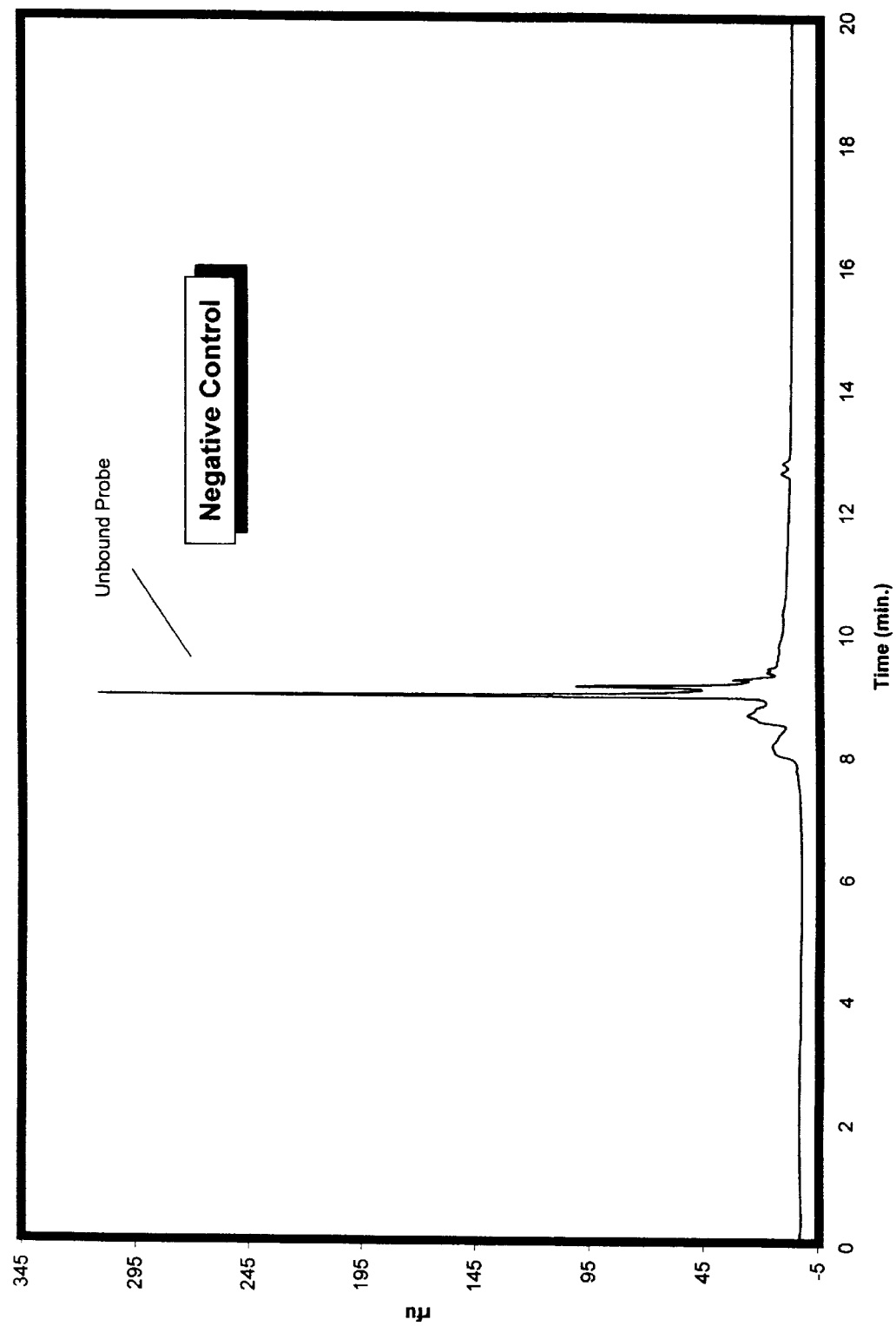
FIGS. 4A and 4B show electropherogram analysis of DNA/DNA hybridization products.
Figure 4B:
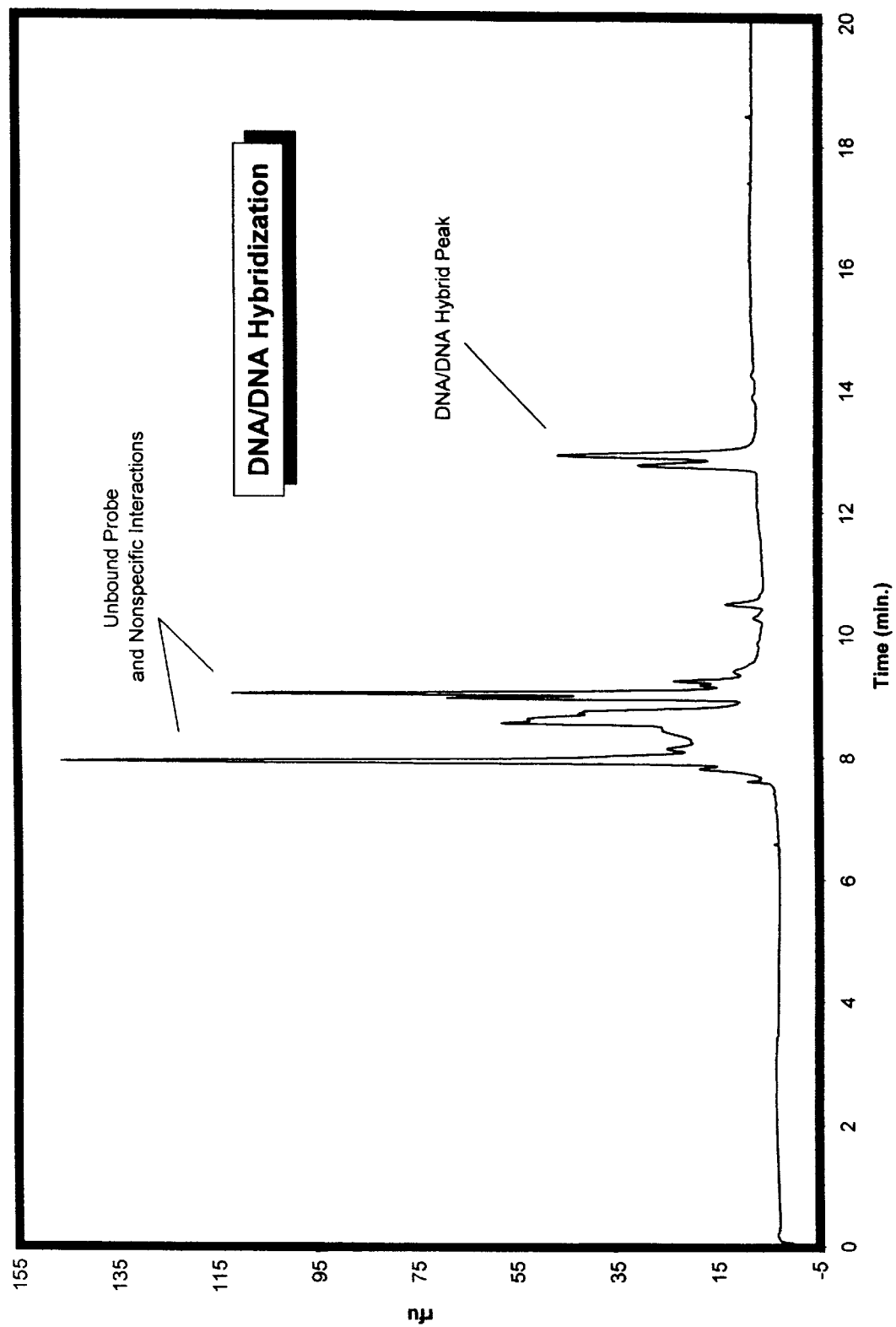

Results of electropherogram analysis of samples from the HIV seropositive patient and the seronegative volunteer hybridized with the HIV specific probe are shown in FIG. 3A–3C. FIG. 3A represents a HIV RNA/Probe complex which elutes at 12 min, indicating the presence of HIV RNA in the patient's serum. FIG. 3B represents a seronegative volunteer. FIG. 3C is a negative control containing all reaction components except RNA.

Referring to Table 1, the stabilities of various calibrator RNA standards are given. The low CV percentages indicate that CE is highly precise with respect to variation both in terms of total fluorescence (peak area) and migration time on the gel.

TABLE 1

Stability of Cellular RNA at Room Temperature

| Peak Area | | | | | |
|---|---|---|---|---|---|
| Peak Injection | 5 S | 16 S | 18 S | 23 S | 28 S |
| Time: 0 | 1523 | 2891 | 586 | 2717 | 921 |
| Time: 30 min | 1277 | 2605 | 650 | 2368 | 1002 |
| Time: 60 min | 1371 | 2603 | 598 | 2183 | 911 |
| Mean | 1390.33 | 2699.67 | 611.33 | 2422.67 | 944.67 |
| St. dev. (±) | 124.13 | 165.70 | 34.02 | 271.1 | 49.9 |
| CV % | 8.9 | 6.1 | 5.5 | 11 | 5 |
| % change over 30 min | −17 | −10 | +10 | −13 | −8 |
| % change over 60 min | −10 | −10 | +2 | −20 | −1 |
| Migration Time | | | | | |
| Injection | | | | | |
| Time : 0 | 11.96 | 12.17 | 13.45 | 14.58 | 16.68 |
| Time : 30 min | 11.94 | 12.21 | 13.44 | 14.54 | 16.64 |
| Time : 60 min | 11.94 | 12.20 | 13.45 | 14.55 | 16.66 |
| Mean | 11.95 | 12.19 | 13.45 | 14.56 | 16.66 |
| St. dev. (±) | 0.012 | 0.021 | 0.006 | 0.021 | 0.02 |
| CV % | 0.1 | 0.1 | 0.04 | 0.1 | 0.1 |

Table 2 compares the detection limits and reproducibility for duplex combinations of RNA/RNA, RNA/DNA, and DNA/DNA. The lower detection limit for DNA/DNA is explained by the greater known number of dye molecules intercalating that duplex than for RNA/RNA. All CV values were less then 15%.

TABLE 2

Comparison of Detection Limits and Reproducibility of Various Nucleotide Complexes

| Nucleotide Complex | Minimum Detectable Quantity | | Precision | |
|---|---|---|---|---|
| | Weight | HIV equivalents | Migration Time CV % | Peak Area CV % |
| RNA/RNA | 500 fg | 50,000 | 0.16–1.1 | 0.9–1.0 |
| DNA/DNA-Fluorescein | 36 ag | 4 | 0.18–0.22 | 7.3–11 |
| DNA/RNA-Fluorescein | 190 ag | 21 | 0.18–0.22 | 5.6–7.3 |

Table 3 shows that the total fluorescence when both a terminal dye (fluorescein (FL)) and an intercalating dye (thiozale orange (TO)) are used is additive when emission takes place at the same wavelength. The stability data show the dramatic contribution to duplex stability of the dye combination.

TABLE 3

| Dye | Peak Area (rounded to nearest 10,000 rfu) | |
|---|---|---|
| 1. Synergy Experiment: DNA/DNA hybrids | | |
| FL alone | 90,000 | |
| TO alone | 10,000 | |
| FL + TO | 100,000 | |
| Complex | Degradation (% decrease in peak area) | Retention time CV |
| 2. Stability Experiment: DNA/RNA hybrids | | |
| FL + TO | <5% | <0.5% |
| FL | 41–45% | >70% |
| TO | 31–33% | 1% |

EXAMPLE 2

Analysis of Low Copy HIV RNA by Addition of Carrier RNA.

Serum obtained from HIV seropositive patient #31 was serially diluted with sterile double distilled $H_2O$. The original sample contained $5 \times 10^5$ HIV copies per mL and five dilutions were made, the most dilute containing 10 copies of HIV RNA per mL. *E. coli* tRNA (100 µg) was added to the diluted samples. RNA was then extracted by Ultraspec II RNA Isolation System, hybridized to labeled probe as usual and analyzed by CE-LIF.

Table 4 below shows detectable total fluorescence using additional carrier RNA and demonstrate no stabilization of the hybrid in the presence of carrier.

TABLE 4

| Copies HIV per mL serum | Weight equivalent | Peak Area (ND = not detectable) |
|---|---|---|
| $5 \times 10^5$ | 50 pg | 9768 |
| $10^5$ | 10 pg | 2437 |
| $10^4$ | 1 pg | ND |
| $10^3$ | 100 fmt | ND |
| $10^2$ | 10 fmt | ND |
| 10 | 1 fmt | ND |

EXAMPLE 3

Direct Detection of DNA

Sample Collection and DNA Extraction

DNA was obtained from A549 cells (negative control) and A549 cells infected with AD-36 (positive control). DNA was extracted from plasma samples using the Qiagen QIAmp blood or tissue isolation system (Qiagen, Valencia, Calif., USA) as recommended by the manufacturer. DNA was resuspended in DEPC-treated water (Biotecx, Houston, Tex., USA) and quantitated spectrophotometrically.

Probe Synthesis and Hybridization

As explained hereinbefore, to ensure specificity, a unique gene sequence was probed. Uniqueness was verified by a GenBank search. Unlabeled and 5'-fluorescein phosphoramidite ($\lambda$=488 nm) labeled DNA probes (probe sequence 5'-AGTTGAAACAGCAAGAGACTCAAAG-3' (SEQ ID NO:14) were synthesized by IDT Laboratories (Coralville, Iowa, USA).

Genomic DNA was adjusted to a concentration of 0.5 µg/19.7 µL and digested with 6 units of Mbol (Promega, Madison, Wis., USA) for 2 hours at 37° C. in the buffer provided by the manufacturer to generate smaller DNA fragments. DNA digests were stored at −20° C. until hybridized. Digested DNA (0.44 µg) was hybridized with the DNA probe (1.25 ng) in a buffer volume of 30 µL containing 10 mM Tris-HCl (pH 7.2), 1 mM EDTA (pH 8.0), 50 mM NaCl, and 1 mM CTAB (ACROS, Pittsburgh. Pa., USA). The mixture was heated at 95° C. for 5 min and then incubated at 53° C. for 6 h.

Following incubation, S1 Nuclease (2.25 U) (Promega, Madison, Wis., USA) and 0.3 M MgCl2 (Promega, Madison, Wis., USA) were added and samples were digested for 20 min at 37° C. to destroy single stranded nucleic acids. The reaction was stopped by the addition of 0.4 M EDTA and samples were stored at 4° C. until analysis.

CE-LIF Analysis.

Separations were performed on a P/ACE 2050 CE system (Beckman Coulter, Inc, Fullerton, Calif., USA) with the temperature held constant at 20° C. Detection of hybrids was achieved using laser-induced fluorescence in the reversed-polarity mode (with the anode at the detector side) at excitation of 488 nm and emission of 520 nm. The sieving polymer solution (sieving polymer provided by Beckman Coulter Inc.) consisted of 25 mM MOPS-TRIS, pH 7.55, containing 0.5% polyethylene oxide (PEO, manufactured by Union Carbide) (mol. wt. $4 \times 10^6$) and 0.4% PEO (mol. wt. $0.9 \times 10^6$). The cathode buffer was prepared by adding 4 µL of thiazole orange intercalator per 10 mL of gel. The capillary was rinsed with the polymer solution and cathode buffer for three minutes prior to each injection. Samples were introduced hydrodynamically by ten second injections at 0.34 Pa across a 27 cm×75 µm i.d. capillary, pretreated with the polymer solution. A ten-second water plug was injected prior to each sample. Separations were performed under constant voltage at 5.4 kV for 15 min. The capillary was calibrated with the fluorescently labeled probe and a mixture of DNA molecular markers (Promega, Madison, Wis., USA). The markers ranged in size from 36–2416 bp. Post-run analysis of data was performed using the System Gold chromatography data system (Beckman Coulter, Inc).

The results of the foregoing method and other determinations are as follows:

Comparison of Molecular Weight to Copy Number

One copy of AD-36 DNA consisted of approximately 33,068 base pairs (bp). Thus, one picogram (pg) of DNA contained $9 \times 10^8$ bp, making one picogram equal to approximately 27,216 copies and one attogram (ag) approximately equal to 0.027 copies of AD-36 DNA.

Determination of the Injection Volume

Based on literature values and applicant's own previous work, the injection volume is 7.1 nL when a sample is injected onto a 100 µm i.d. capillary at 0.34 Pa for 10 seconds. For a 75 µm i.d. capillary, an injection volume of 5.14 nL for 10 seconds at 0.34 Pa was calculated. This injection volume was verified for the present system, using the 75 µm i.d. capillary, by measuring the mass difference after injection. 40 µL of hybridization sample was placed in four separate microcuvettes and weighed on a Ohaus GA200D balance. Samples 1 and 2 were designated as the injection vials and samples 3 and 4 were used as controls for evaporation. After weighing, the microcuvettes containing the sample were transferred to the auto-sampler tray and injected hydrodynamically at 0.34 PA for 990 sec (99 seconds ×20 injections, 99 second maximum injection time). The microcuvettes were then re-weighed with a mean decrease in weight after injection of 1050 µg (n=3). Since the hybridization solution was very dilute, it was assumed to have the specific gravity of water (1.00 g/mL), corresponding to a mean volume of 1050 nL per 1980 second injection or of 5.19±0.548 nL per 10 second injection (n=3).

Non-Specific Analysis of AD-36 by Total DNA Content and Restriction Digest

It was anticipated that the AD-36 infected A549 cells would contain more DNA than uninfected A549 cells, indicating the presence of AD-36. To determine if the DNA concentration varied between AD-36 infected and noninfected cells, cells were counted and $2 \times 10^6$ were aliquoted into fractions for extraction. DNA was isolated, resuspended in ddH$_2$O water and quantitated spectrophotometrically.

The A549 cells infected with AD-36 contained a mean concentration of DNA of 1.67 µg/nL (n=5). In comparison, the uninfected A549 cells had 1.94 µg/nL (n=5) and there was no significant difference in DNA concentration (p=0.38). These data indicate that the AD-36 viral DNA comprises a small fraction of the total cellular DNA, and that comparison of DNA concentrations between infected and noninfected cells is not sensitive enough to identify the presence of AD-36 DNA.

Because the AD-36 DNA sequence differs from the genomic A549 DNA sequence, it was expected that a restriction digest would produce a different digest pattern in AD-36 infected A549 cells when compared to the uninfected A549 cells and would permit distinguishing AD-36 by restriction digest.

DNA from AD-36 infected A549 cells and uninfected A549 cells was isolated and digested with Mbol and analyzed by CE-LIF. As described hereinbefore, thiazole orange present in the CE buffer system intercalates dsDNA, detecting any double stranded DNA, including both genomic A549 and viral AD-36 DNA. No difference in restriction pattern between the infected and uninfected cells was observed. These data indicate that AD-36 DNA represented a small fraction of the total cellular DNA and is indistinguishable from the total population when analyzed by this method.

Specific Analysis of AD-36 by Labeled and Unlabeled Probes

To identify AD-36, a unique probe sequence was synthesized and hybridized to target DNA to generate probe:AD-36 nucleotide complexes. As described hereinbefore, detection of these complexes by CE-LIF depends on detection of fluorescence signals from complexes separated by CE-LIF. Thiazole orange present in the buffer intercalates into one of every two DNA bp and fluoresces when bound, representing a single detection system. 5' labeling of probes with fluorescein generates an additional signal and in combination with thiazole orange represents a dual detection system.

Analysis of the Probe Alone

Fluorescently labeled and unlabeled probes unique to the AD-36 virus were synthesized. The probe sequences were identical, the only difference being a 5' fluorescein. The probes contain the sequence TTGA at the 5' end that may bind to the AACT located at the 3' end, forming a double stranded structure which can be intercalated by thiazole orange.

To determine the migration time of the probe, both unhybridized and hybridized, labeled and unlabeled probes were analyzed. The labeled and unlabeled probes were hybridized as described above, but without target DNA. The final concentration for analysis of both the hybridized and unhybridized probes was 4 µg/µL.

In accordance with the present invention, all dsDNA sequences can be intercalated by thiazole orange, and thus generate a fluorescent signal. When the unhybridized, unlabeled, probe was analyzed, no peaks were identified. This result showed that probe self-binding does not occur without hybridization conditions. Both the unhybridized, labeled probe and the hybridized, unlabeled probe generated a single peak eluting between 4 and 5 minutes. Migration time and peak areas for these samples were variable, with both the peak area precision and migration time precision >150%. Considered separately, these samples had a single detection system (either thiazole intercalation or 5' fluorescein). It is possible that the large CV's obtained in each case resulted from instability of the detected molecule.

The labeled, hybridized, probe generated one peak, eluting at 6.61 minutes, the migration time of the self-bound probe. This probe complex was stable with peak area and migration time CV's of 2.65 and 1.65, respectively. Minimal detectable quantity of the labeled probe was 10.3 fg/nL, corresponding to 282 copies of AD-36 DNA. (signal-to-noise ratio 3:1) (see, Table 5).

These data indicate that analysis by the dual detection system provides increased stability over the single detection system alone. The thiazole orange intercalates the nucleotide complexes, which may inhibit the dissociation of the complex when the high electrical field of CE-LIF is applied. The terminal fluorescein also contributes to complex stability, perhaps by protecting the 5' end from free solution hydrolysis.

Analysis of AD-36 by Labeled and Unlabeled Probe

Figure 5:
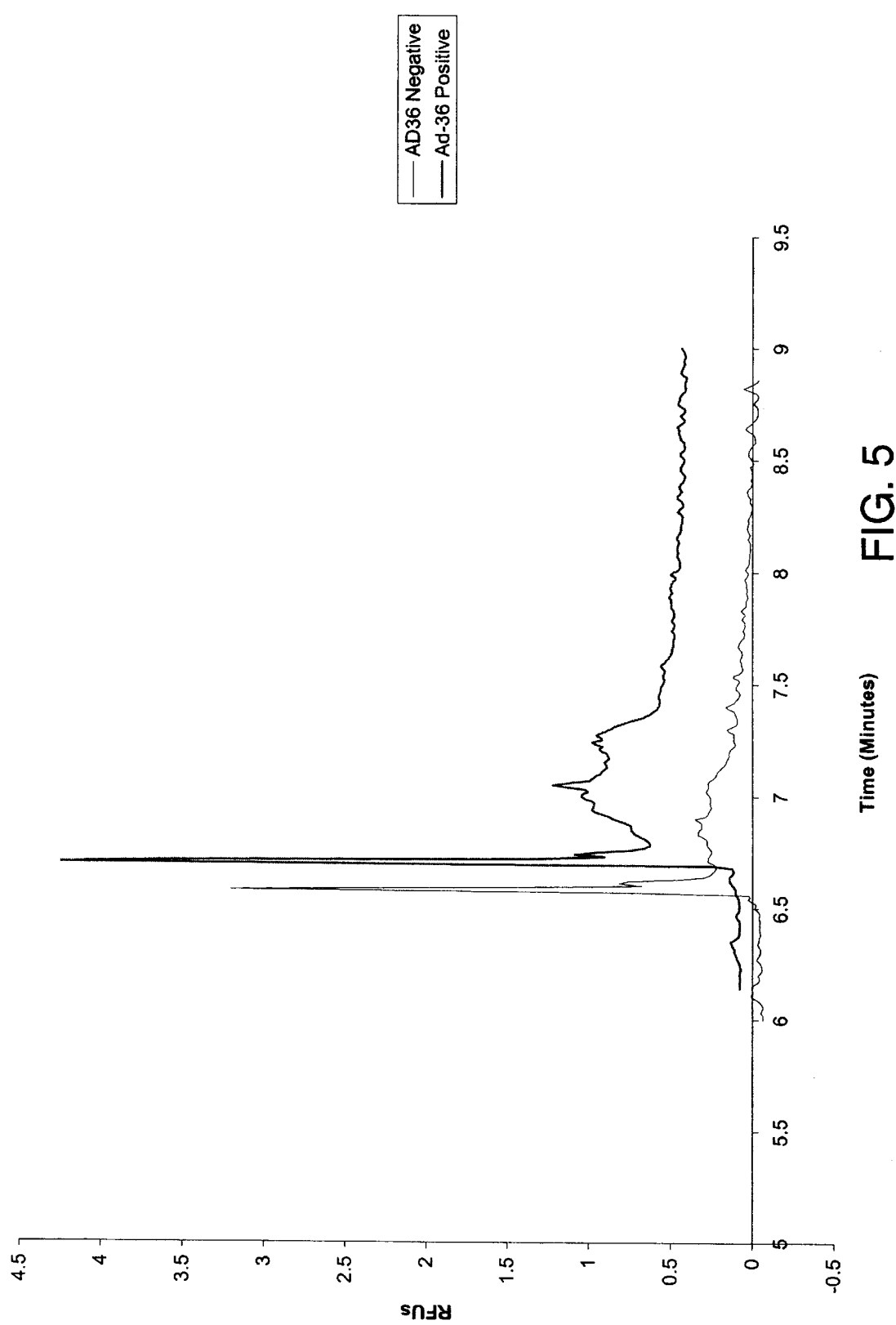
FIG. 5 shows electropherograms of nucleic acid (total DNA) from AD-36 infected and noninfected A549 cells hybridized with an AD-36-specific unlabeled probe.
Figure 6:
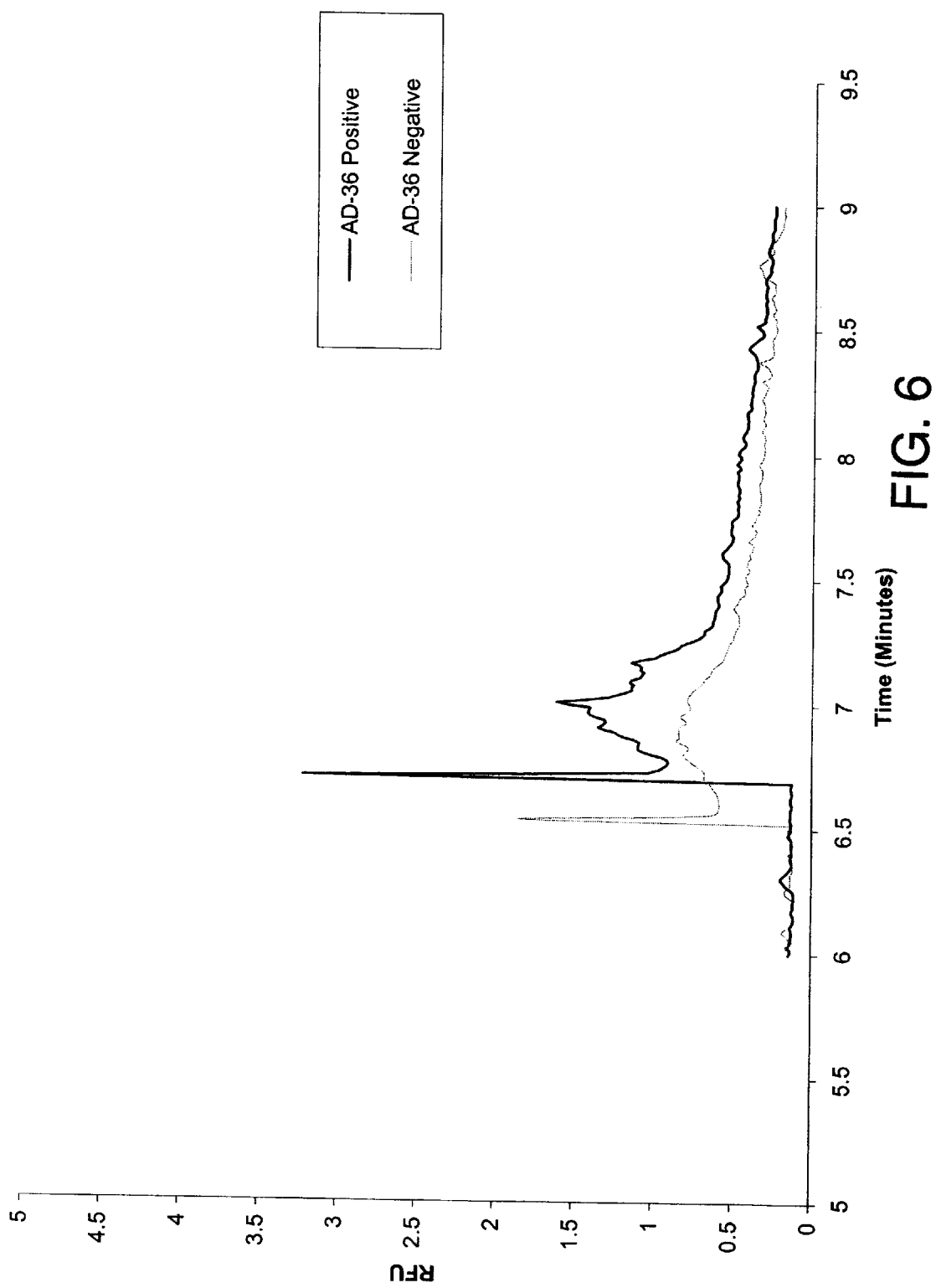
FIG. 6 shows electropherograms of nucleic acid (i.e., total DNA) from AD-36 infected and noninfected A549 cells hybridized with an AD-36 specific 5' fluorescently labeled probe.
Figure 7:
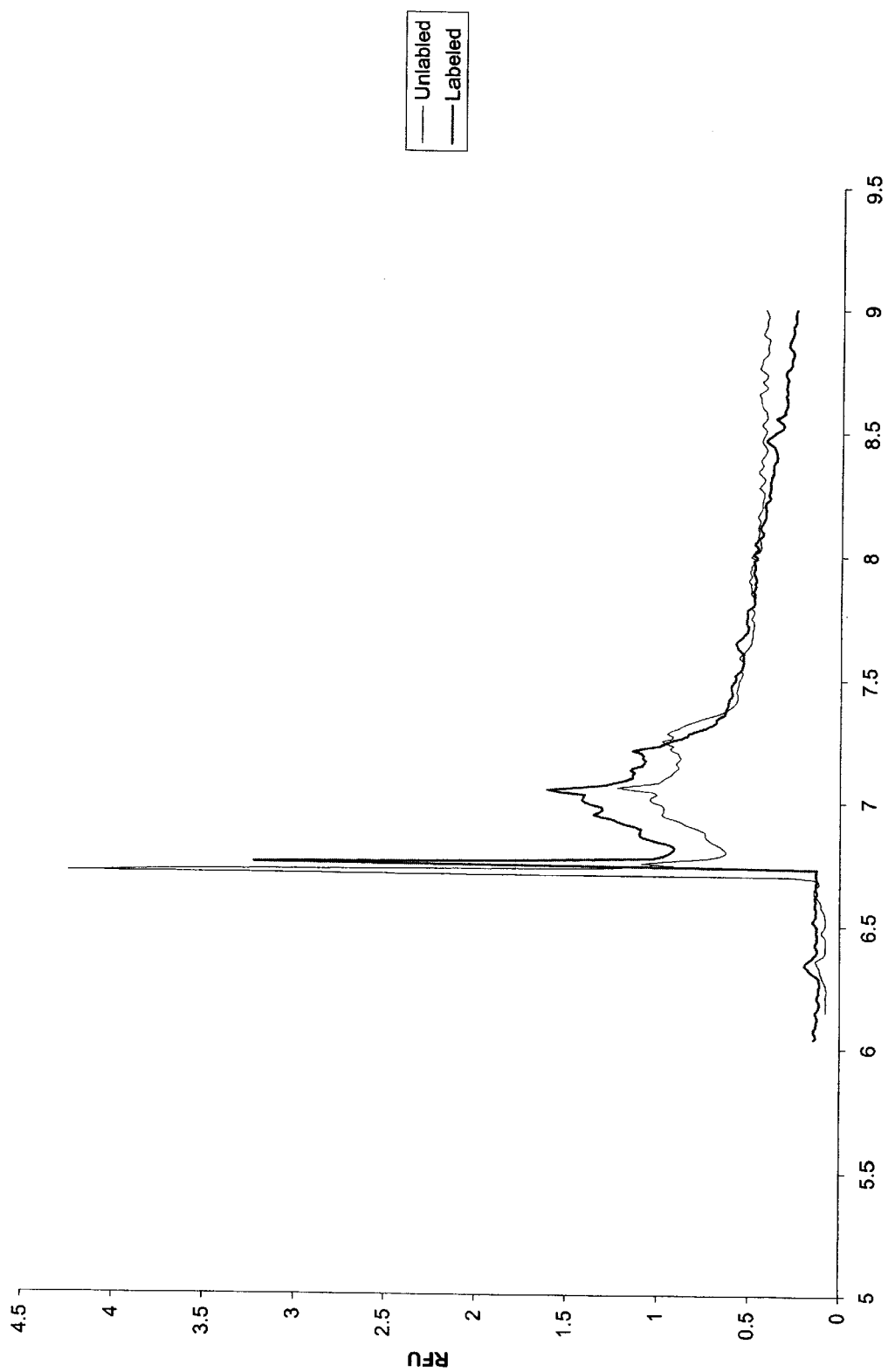
FIG. 7 is an electropherogram comparing labeled and unlabeled AD-36-specific probe hybridized to total DNA from AD-36-positive A549 cells and electrophoresed in the presence of thiazole orange.

Both the AD-36 infected and uninfected A549 cells were hybridized with labeled and unlabeled AD-36 probes. FIG. 5 shows electropherogram analysis with the AD-36-specific unlabeled probe. The first peak eluted at approximately 6.54 minutes in the AD-36 negative cells and 6.71 minutes in the AD-36 positive cells represents the self-bound probe complex. A mass effect, where increased nucleic acid binding slightly prolongs migration time, may explain the slightly prolonged migration times in the AD-36 positive cells. The second peak eluting at 7.01 minutes is present only in the AD-36 positive cells and represents viral DNA. FIG. 6 shows electropherogram analysis with the AD-36 specific labeled probe. The first peak eluting at approximately 6.6 minutes in the AD-36 negative cells and 6.7 minutes in the AD-36 negative cells represents the self-bound probe complex. The second peak eluting at approximately 7 minutes is present only in the AD-36 positive cells and represents viral DNA. FIG. 7 shows electropherogram analysis comparing the 5' fluorescently labeled and the unlabeled AD-36 specific probes in the presence of thiazole orange. The first peak in both samples elutes at approximately 6.7 minutes and is the self-bound probe. The second peak eluting for both samples at approximately 7 minutes is the AD-36 DNA. The unlabeled probe relies on a single detection system, the thiazole orange present in the buffer system which intercalates double stranded DNA and provides the signal. The labeled probe has a dual detection system, both the thiazole orange and the fluorescent label.

Peak areas and migrations time for AD-36 infected A549 cells hybridized with the labeled probe and unlabeled probe from FIG. 7 were compared to determine the contribution of the terminal fluorescein over thiazole orange detection alone. The terminally-labeled fluorescein complexes (fluorescein+thiazole orange detection) generated a mean total peak area of 275.79±16.59 (n=3) compared to that generated by the unlabeled probe (thiazole orange detection only) of 163.14±20.81 (n=3), corresponding to a 59% increase in signal.

For the fluorescein-labeled probe hybridizations, the intra-day and inter-day migration time precision was 1.13% and 0.82% (n=6), respectively. The intra-day peak area precision was 6.0%(n=6) and the inter-day peak area precision was 31.84%. For the unlabeled hybridizations, the intra-day and inter-day migration time precision was 1.61% and 1.73% (n=6), respectively. The intra-day peak area precision was 12.8%(n=6) and the inter-day peak area precision was 28.74%.

The fluorescein label, in addition to improving the sensitivity of the assay, also improved the reliability, decreasing the inter-day variability from 12.8% to 6.0%. The samples were stored at 4° C. during the inter-day validation period. Because the inter-day precision was poor at 4° C., all samples are now run immediately after hybridization.

TABLE 5

Inter-day and Intra-day Validation of Labeled, Unlabeled and Self-Bound Probe

| Intra-day Precision-Day 1 | AD36: Labeled probe complex | AD36: Unlabeled probe complex | Self-Bound Probe (labeled) |
|---|---|---|---|
| Migration Times | | | |
| Mean | 6.93 | 6.91 | 6.61 |
| Standard Deviation | 0.08 | 0.11 | 0.11 |
| CV % | 1.13 | 1.61 | 1.65 |
| Peak Area (Total) | | | |
| Mean | 275.79 | 163.14 | 152.85 |
| Standard Deviation | 16.59 | 20.81 | 4.05 |
| CV % | 6.02 | 12.76 | 2.65 |
| Migration Time | | | |
| Mean | 6.68 | 6.65 | 6.55 |
| Standard Deviation | 0.06 | 0.12 | 0.13 |
| CV % | 0.82 | 1.73 | 2.05 |
| Mean | 204.53 | 128.22 | 86.41 |
| Standard Deviation | 65.12 | 36.87 | 58.46 |
| CV % | 31.84 | 28.75 | 67.66 |

EXAMPLE 3

Deletion Mutation Analysis

DNA from the MCF7 and LNCaP cell lines was compared. The MCF7 is an NQO1 overexpressing cell line, while the LNCaP cell line is a prostate cancer cell line with a large deletion on chromosome 16 where NQO1 is located.

Sample Collection and Extraction

DNA from both cell lines was isolated using the Wizard Genomic DNA Purification Kit (cat. #A1120) from Promega, Madison, Wis. and the Ultraspec II RNA isolation system (Biotecx, Houston, Tex.) as instructed by the manufacturers. The DNA was digested with MboI restriction enzyme (cat. #R6711) from Promega following the product usage information.

Probe Synthesis and Hybridization

Digested DNA from each cell line was hybridized to a 5' fluorescein labeled probe synthesized by Integrated DNA Technologies, Inc., Coralville, Iowa. As explained hereinbefore, to ensure specificity, a unique gene sequence was probed. Uniqueness was verified by a GenBank search. A 22-bp probe having the sequence: 5' ATTTGAAT-TCGGGCGTCTGCTG 3' (SEQ ID NO:15) was mixed with the DNA at a probe/DNA ratio of 1/80, into a buffer containing 10 mM Tris-HCl, 1 mM EDTA, 50 mM NaCl, and 1 mM CTAB. A control contained the same quantity of probe and buffer, substituting sterile, distilled, deionized water (dd $H_2O$ for the DNA solution. The mixtures were heated to 95° C. for five minutes to denature the strands, and then incubated overnight at 59° C. to anneal.

CE-LIF Analysis

Separations were performed on a P/ACE 2050 CE system (Beckman Instruments, Fullerton, Calif., USA) with the temperature held constant at 20° C. Detection of hybridization samples was achieved using laser-induced fluorescence in the reversed-polarity mode (anode at the detector side) at excitation of 488 nm and emission of 520 nm. Samples were introduced hydrodynamically by 10 s injections at 0.34 Pa across a 65 cm×100 μm coated eCAP dsDNA capillary filled with replacable linear polyacrylamide (Beckman Instruments, Fullerton, Calif., USA). The capillary was conditioned with eCAP dsDNA 1000 gel buffer which contained 60 μL of LiFluor dsDNA 1000 EnhanceCE (thiazole orange) intercalator per 20 mL of gel buffer (Beckman Instruments, Fullerton, Calif., USA). Separations were performed under constant voltage at 7.0 kV for 15–30 min. The capillary was rinsed with gel buffer for 3 min prior to each injection. The capillary was calibrated with the fluorescently labeled probe and a mixture of RNA molecular markers (Ambion, Austin, Tex., USA). The five markers ranged in sized from 100–500 bp. Post-run analysis of data was performed using the System Gold chromatography data system (Beckman Instruments, Fullerton, Calif., USA).

Figure 8:
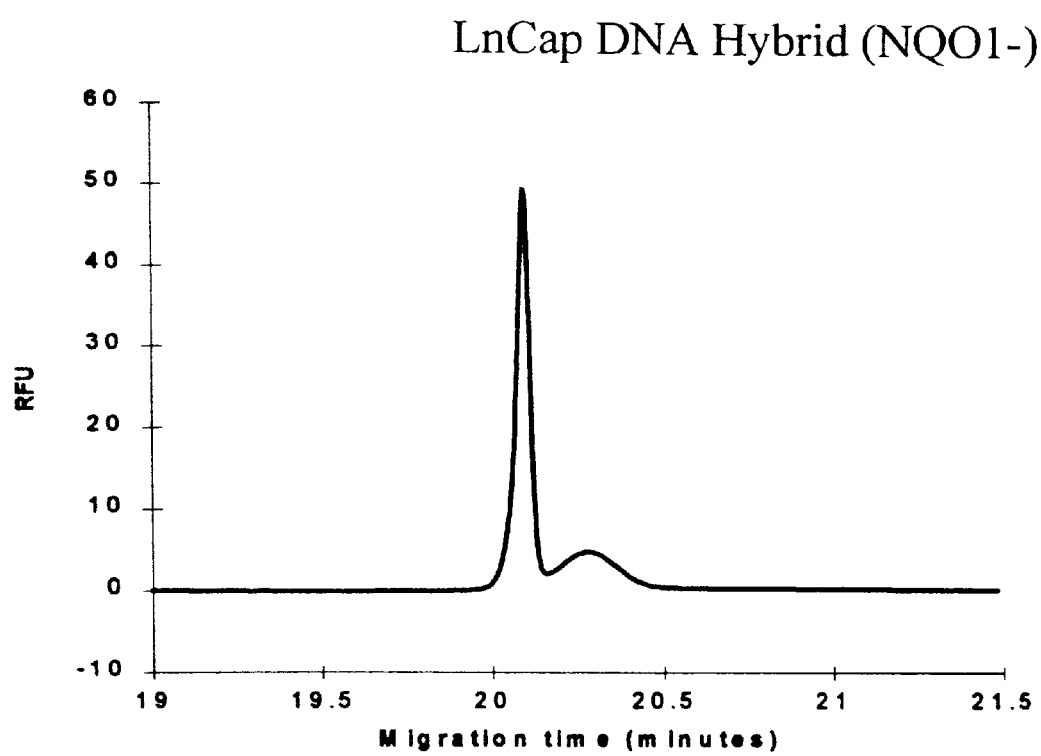
FIG. 8 is an electropherogram showing the migration time of an unbound NQO1-specific probe in the presence of DNA lacking the NQO1 sequence.
Figure 9:
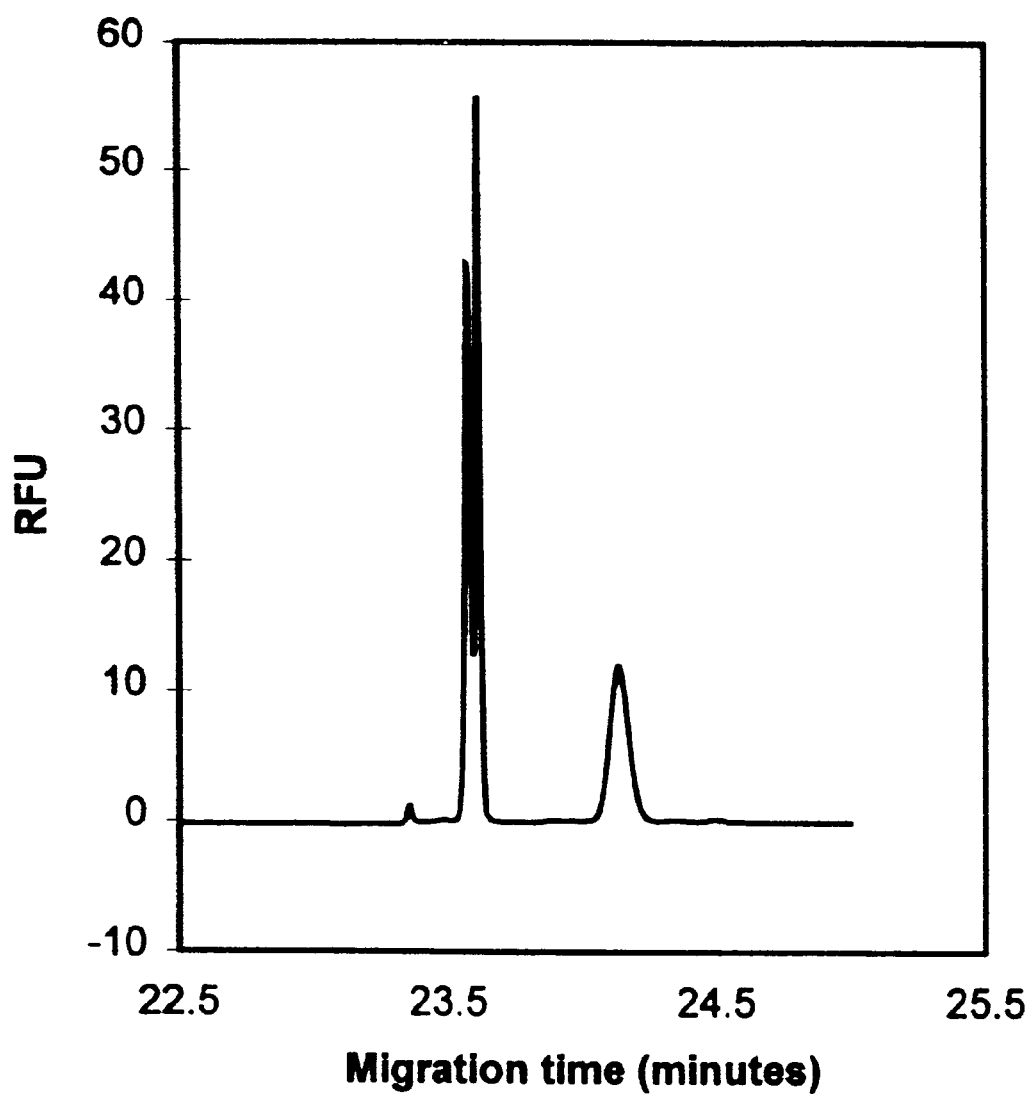
FIG. 9 is an electropherogram which shows migration of unbound NQO1-specific probe and NQO1-specific probe bound to a NQO1 target gene sequence.

When DNA obtained from the LnCaP, or NQO1 negative cell line is hybridized with the NQO1 specific probe, a single peak elutes at 20 minutes and indicates the presence of the unbound probe and the absence of NQO1 (see, FIG. 8). When DNA obtained from MCF7, or the NQO1 positive cell line, is hybridized with the NQO1 specific probe, two peaks elute, the first at 23.5 minutes representing the unbound probe and the second, at approximately 24.5 minutes, representing the NQO1 gene (see, FIG. 9). The retention time for the unbound probe is prolonged in the MCF7 samples, likely due to a mass effect of the bound nucleic acid. These electropherograms (FIGS. 8 and 9) show clearly that the NQO1 specific probe binds only NQO1 and can identify the presence of a deletion in the NQO1 gene.

Figure 10:
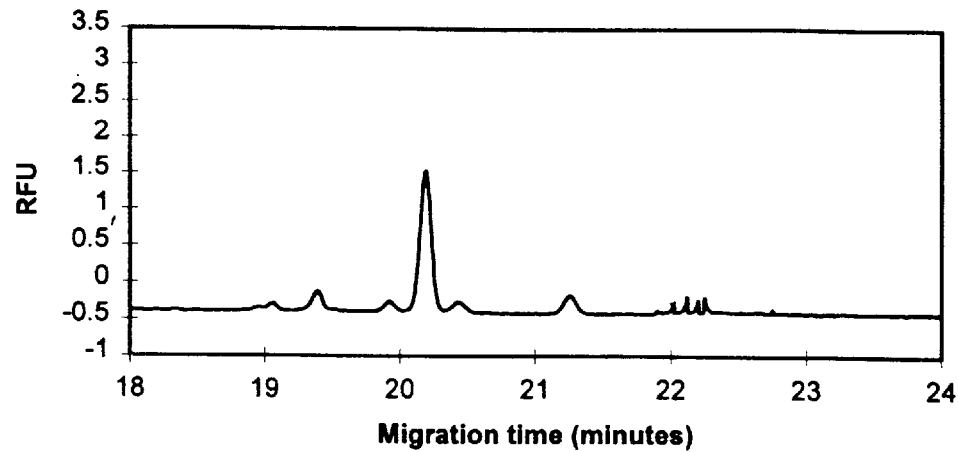
FIG. 10 is an electropherogram showing the migration time of an unbound NQO1-specific probe in the presence of RNA lacking the NQO1 sequence.
Figure 11:
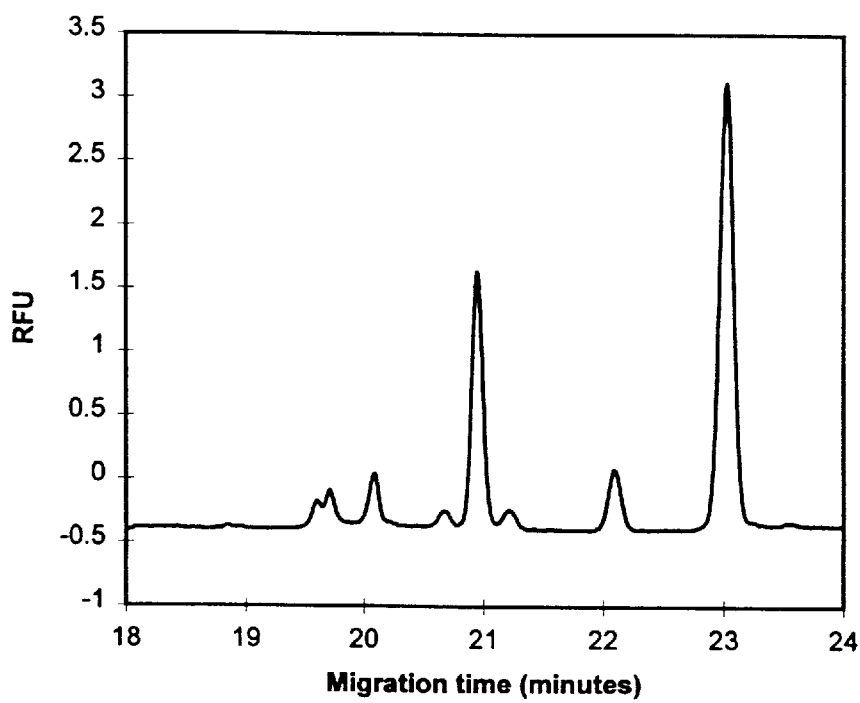
FIG. 11 is an electropherogram which shows migration of unbound NQO1-specific probe and NQO1-specific probe bound to a RNA target sequence.

In addition, electropherograms may also be used to evaluate the presence or absence of mRNA. When RNA obtained from the LNCaP, a NQO1-negative cell line, was hybridized with the NQO1-specific probe, a single peak eluted at 20 minutes, indicating the presence of the unbound probe and the absence of NQO1 (see, FIG. 10). When RNA obtained from MCF7, a NQO1-positive cell line, was hybridized with the NQO1-specific probe, two peaks eluted: the first at 21 minutes representing the unbound probe and the second, at approximately 23.5 minutes, representing the NQO1 gene (see, FIG. 11). The absence of RNA may be due to gene deletion or lack of expression.

EXAMPLE 4

Point Mutation Analysis

General Approach

A characteristic point mutation (a C→T transition) is present in the NQO1 gene at bp609. Two probes of different molecular weights to allow separation by electrophoresis were synthesized to the wild type and the mutant NQO1 gene. A cancer patient had a point mutation at bp 609, which was confirmed by sequencing and RFLP. A normal volunteer had the wild-type NQO1 sequence. Isolated RNA from patient samples was used as a template in RT-PCR to obtain cDNA.

Like deletional analysis, the wild-type probe will bind to the wild-type sequence and the mutant probe will bind to the mutant sequence. Three electropherograms are possible. The first, generating one peak of the wild-type probe only, indicates that the sample is a homozygous wild-type. The second, generating one peak of the mutant probe only, indicates that the sample is homozygous mutant. The third possibility is the presence of two peaks, indicating the presence of both wild-type and mutant gene. Since the assay in accordance with the present invention is quantitative, the peak area of the wild-type to the peak area of the mutant gene was compared and a ratio obtained. A 1:1 ratio indicates a heterozygous sample. Alterations in the ratio from 1:1 indicate the presence of differing amounts of wild-type to mutant.

Sample Collection and Extraction

Blood samples (heparinized-anticoagulated whole blood) were obtained from a cancer patient who gave informed consent and a normal volunteer RNA was extracted from peripheral blood lymphocytes using the Ultraspec II RNA isolation system as recommended by the manufacturer (Biotecx, Houston, Tex.). RNA was resuspended in DEPC-treated water and quantitated spectrophotometrically. RNA was aliquoted in 1ug amounts, and converted to cDNA by the reverse transcription reaction as recommended by the manufacturer.

Probe Synthesis and Hybridization

To differentiate between mutant and wild type sequence, the 609 bp region of NQO1 is probed. To ensure specificity, this sequence must be unique, and uniqueness was verified by a GenBank search. Two 5'-fluorescein phosphoramidite (Glenn Research, Sterling, Va., USA) labeled DNA probes were synthesized by the University of Wisconsin Biotechnology Center. The wildtype probe had the sequence 5'-CCGAAGGTTGAATCTTGGACTTGACTG-3') (SEQ ID NO:16), and the mutant probe had the seqeunce 5'-CCGAAGGTTGAATCTTAGACT TGACTGTATATCGTAA-3' (SEQ ID NO: 17).

Sample cDNA present in a concentration of 0.095 $\mu g/\mu L$ was diluted serially with DEPC-treated water and hybridized with the DNA probes (mutant and wild-type) (1.0125 $\mu g$) in a buffer volume of 30 $\mu L$ containing 10 mM Tris-HCl (pH 7.2), 1 mM EDTA (pH 8.0), 50 mM NaCl, and 1 mM CTAB. The mixture was heated at 85° C. for 10 min, and then incubated at 42° C. for 4 h.

CE-LIF Analysis

Separations were performed on a P/ACE 2050 CE system with the temperature held constant at 20° C. Detection of hybridization samples was achieved using laser-induced fluorescence in the reversed-polarity mode (anode at the detector side) at excitation of 488 nm and emission of 520 nm. Samples were introduced hydrodynamically by 10 s injections at 0.34 Pa across a 65 cm×100 $\mu m$ coated eCAP dsDNA capillary filled with replaced linear polyacrylamide. The capillary was conditioned with eCAP dsDNA 1000 gel buffer which contained 60 $\mu L$ of LiFluor dsDNA 1000 EnhanceCE (thiazole orange) intercalator per 20 mL of buffer. Separations were performed under constant voltage at 7.0 kV for 15–30 min. The capillary was rinsed with gel buffer for 3 min prior to each injection. The capillary was calibrated with the fluorescently labeled probe and a mixture of RNA molecular markers. The five markers ranged in sized from 100–500 bp. Post-run analysis of data was performed using the System Gold chromatography data system.

Figure 12:
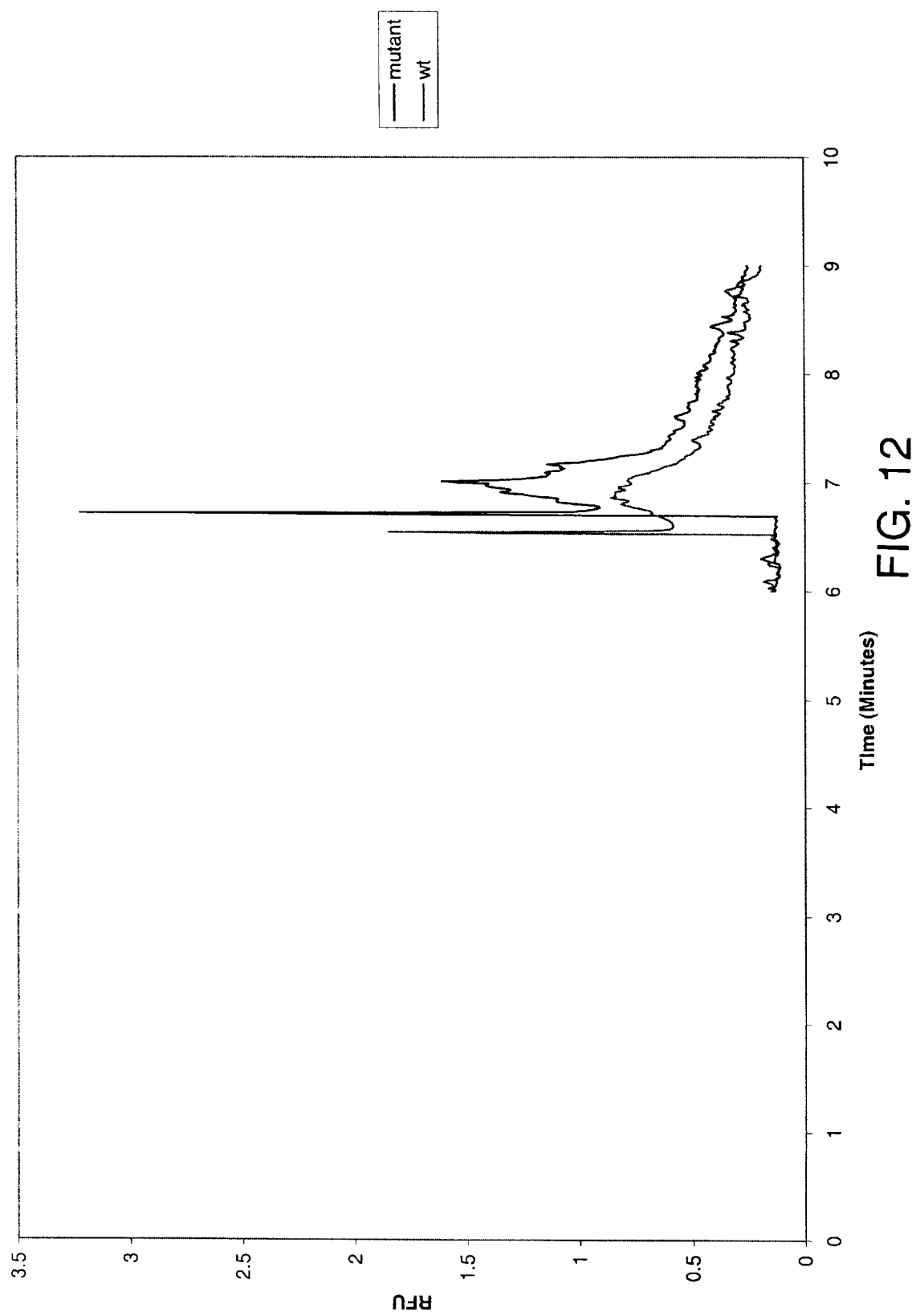
FIG. 12 shows superimposed electropherograms of mutant (cancer patient) and wild-type (wt) NQO1 (normal volunteer) hybridizations.

Reference is made to FIG. 12 which shows superimposed electropherograms of mutant and wild-type NQO1 hybridizations. cDNAs from the two individuals, one with mutant NQO1 (cancer patient) and the other with wild-type NQO1 (normal volunteer) confirmed by sequencing, were hybridized with the wild-type and mutant NQO1 probes, as described above. The wild-type probe binds to the wild-type sequence in the normal volunteer cDNA generating a single peak which elutes at 6.5 minutes. Because cDNA of the volunteer is wild-type, there is no binding of the mutant probe and no second peak. The mutant probe is 10 base pairs longer than the wild-type probe, and therefore, elutes at 6.75 minutes for the cancer patent. Because the cancer patient was homozygous mutant, there is no peak at 6.5 minutes, indicating the absence of wild-type NQO1.

While the present invention has now been described and exemplified with some specificity, those skilled in the act will appreciate the various modifications including variations, additions and omissions, that may be made in what has been described. Accordingly, it is intended that these modifications also be encompassed by the present invention and that the scope of the present invention be limited solely by the broadest interpretation that lawfully can be ascended the appended claims.

What is claimed is:

1. A method for direct detection of a target nucleotide sequence in a sample comprising unamplified nucleic acid molecules comprising the steps of:

(a) mixing a portion of the sample with a fluorescent polynucleotide probe under hybridizing conditions to form hybrids of probe and target sequences, the probe having a nucleotide sequence complementary to at least a portion of the target sequence;

(b) applying a portion of the mixture of step (a) to a capillary electrophoresis column;

(c) electrophoresing the hybrids of step (a) under an electric current applied to the capillary column (b) in the presence of a dye capable of intercalating double stranded nucleic acids the electrophoresis conducted for a period of time and under conditions suitable to allow size fractionation of the hybrids; and (d) measuring the fluorescent intensity of light emitted from the column upon excitation by laser-induced fluorescence.

2. The method of claim 1, wherein the sample comprises nucleic acids selected from the group consisting of RNA and DNA, and combinations thereof.

3. The method of claim 1, wherein the intensity of emitted light is measured continuously as a function of retention time.

4. The method of claim 1, further comprising the step of analyzing the measurements of step (d).

5. The method of claim 1, wherein the target sequence is quantified.

6. The method of claims 1, wherein the dye is selected from the group consisting of thiazole orange and YOYO.

7. The method of claim 1, wherein the polynucleotide probe is selected from group consisting of DNA and RNA.

8. A kit for direct detection of a target nucleotide sequence suspected of being present in a sample using capillary electrophoresis and laser-induced fluorescence, the sample comprising unamplified nucleic acid isolated from a biological source, the kit comprising a polynucleotide probe, the probe terminally labeled with a fluorophore at the 5' end and having a sequence complementary to at least a portion of the target nucleotide sequence, and a dye capable of intercalating nucleic acid hybrid molecules.

9. A method for direct detection of a gene sequence in a sample comprising unamplified nucleic acid isolated from a biological source, comprising the steps of:

(a) mixing under hybridizing conditions a portion of the sample with a fluorescent polynucleotide probe, the probe comprising a fluorescent polynucleotide probe complementary to at least a portion of the gene sequence to form hybrids of probe and target sequences;

(b) applying a portion of the mixture of step (a) to a capillary electrophoresis column;

(c) electrophoresing the hybrids of step (a) in the capillary column of step (b) under an electric current applied to the capillary column in the presence of a dye capable of intercalating double stranded nucleic acids, the electrophoresis conducted for a period of time and under conditions suitable to allow size fractionation of the hybrids; and (d) measuring the fluorescent intensity of light emitted from column upon excitation by laser-induced fluorescence.

10. The method of claim 9, wherein the intensity of emitted light is measured continuously as a function of retention time.

11. The method of claim 9, further comprising the step of:

(e) analyzing the measurements of step (d).

12. The method of claim 9, wherein the analyzing step allows determination of the presence or absence of the target sequence.

13. The method of claim 9, wherein the target sequence is quantified.

14. A method for directly detecting the presence or absence of a point mutation in a target sequence in a sample comprising unamplified nucleic acid molecules isolated from a biological source, comprising the steps of:

(a) mixing a portion of the sample with a polynucleotide probe comprising a first fluorescent polynucleotide probe complementary to a mutated target sequence under hybridizing conditions to form hybrids of probe and target sequence;

(b) applying a portion of the mixture of step (a) to a capillary electrophoresis column;

(c) electrophoresing the hybrids in the capillary column of step (b) in the presence of a dye capable of intercalating double stranded nucleic acids, the electrophoresis conducted for a period of time and under conditions suitable to allow size fractionation of the hybrids; and (d) measuring the fluroscent intensity of light emitted from column upon excitation by laser-induced flurorescence.

15. The method of claim 14, wherein the intensity of emitted light is measured continuously as a function of retention time.

16. The method of claim 14, further comprising the step of:

(e) analyzing the measurements of step (d).

17. The method of claim 14, wherein the target sequence is quantitated.

18. The method of claim 14, wherein the probe preparation further comprises a second fluorescent polynucleotide probe complementary to the wild-type sequence corresponding to the mutated sequence, the length of the second probe being different from the length of the first probe.

19. A method for stabilizing during capillary electrophoresis nucleic acid hybrids comprising a polynucleotide target strand and a fluorophore terminally-labeled polynucleotide probe strand comprising electrophoresing said nucleic acid hybrids in the presence of a dye capable of intercalating double stranded nucleic acids.

* * * * *